(12) United States Patent
Bai et al.

(10) Patent No.: US 11,794,039 B2
(45) Date of Patent: Oct. 24, 2023

(54) MULTIMODAL RADIATION APPARATUS AND METHODS

(71) Applicant: Accuray, Inc., Sunnyvale, CA (US)

(72) Inventors: Chuanyong Bai, Solon, OH (US); Zhicong Yu, Highland Heights, OH (US); Chuang Miao, Sunnyvale, CA (US)

(73) Assignee: Accuray, Inc., Sunnyvale, CA (US)

( * ) Notice: Subject to any disclaimer, the term of this patent is extended or adjusted under 35 U.S.C. 154(b) by 0 days.

(21) Appl. No.: 17/374,618

(22) Filed: Jul. 13, 2021

(65) Prior Publication Data
US 2023/0017353 A1     Jan. 19, 2023

(51) Int. Cl.
*A61B 6/00* (2006.01)
*A61N 5/10* (2006.01)

(52) U.S. Cl.
CPC ......... *A61N 5/1082* (2013.01); *A61N 5/1043* (2013.01); *A61N 5/1047* (2013.01); *A61N 5/1049* (2013.01); *A61N 2005/1052* (2013.01)

(58) Field of Classification Search
None
See application file for complete search history.

(56) References Cited

U.S. PATENT DOCUMENTS

| | | |
|---|---|---|
| 4,190,773 A | 2/1980 | Braden et al. |
| 5,615,279 A | 3/1997 | Yoshioka et al. |
| 6,233,478 B1 | 5/2001 | Liu |
| 6,307,909 B1 | 10/2001 | Flohr et al. |
| 7,050,528 B2 | 5/2006 | Chen |
| 7,108,421 B2 | 9/2006 | Gregerson et al. |
| 7,433,443 B1 | 10/2008 | Tkaczyk et al. |
| 7,660,380 B2 | 2/2010 | Boese et al. |
| 8,116,430 B1 | 2/2012 | Shapiro et al. |
| 8,467,497 B2 | 6/2013 | Lu et al. |
| 8,588,363 B2 | 11/2013 | Flohr |

(Continued)

FOREIGN PATENT DOCUMENTS

| | | |
|---|---|---|
| DE | 102006007058 A1 | 7/2007 |
| EP | 1062914 A1 | 12/2000 |

(Continued)

OTHER PUBLICATIONS

Wang et al., A General Cone-Beam Reconstruction Algorithm, IEEE Transactions on Medical Imaging, Sep. 1993, pp. 486-496, vol. 12, No. 3.

(Continued)

*Primary Examiner* — Hoon K Song
(74) *Attorney, Agent, or Firm* — Calfee, Halter & Griswold LLP

(57) ABSTRACT

An imaging apparatus comprises a rotatable gantry system positioned at least partially around a patient support; a first source of radiation coupled to the rotatable gantry system, the first source of radiation configured for imaging radiation; a second source of radiation coupled to the rotatable gantry system; and a first radiation detector coupled to the rotatable gantry system and laterally movable relative to a central beam of the first source of radiation to receive radiation from at least the first source of radiation over various fields of view. Alternative configurations of the imaging apparatus and methods of using the imaging apparatus are also provided.

17 Claims, 10 Drawing Sheets

(56) References Cited

U.S. PATENT DOCUMENTS

| | | |
|---|---|---|
| 9,400,332 B2 | 7/2016 | Star-Lack et al. |
| 9,952,164 B2 | 4/2018 | Wiedmann et al. |
| 2003/0007601 A1 | 1/2003 | Jaffray et al. |
| 2003/0076927 A1 | 4/2003 | Nakashima et al. |
| 2004/0068169 A1 | 4/2004 | Mansfield et al. |
| 2004/0091079 A1 | 5/2004 | Zapalac |
| 2004/0102688 A1 | 5/2004 | Walker et al. |
| 2004/0202360 A1 | 10/2004 | Besson |
| 2005/0053188 A1 | 3/2005 | Gohno |
| 2005/0251029 A1 | 11/2005 | Khamene et al. |
| 2006/0104496 A1 | 5/2006 | Arenson et al. |
| 2006/0109954 A1 | 5/2006 | Gohno |
| 2006/0262894 A1 | 11/2006 | Bernhardt et al. |
| 2007/0127621 A1 | 6/2007 | Grass et al. |
| 2007/0189444 A1 | 8/2007 | Van Steven-Daal et al. |
| 2008/0112532 A1 | 5/2008 | Schlomka |
| 2009/0080603 A1 | 3/2009 | Shukla et al. |
| 2009/0135994 A1 | 5/2009 | Yu et al. |
| 2009/0161826 A1 | 6/2009 | Gertner et al. |
| 2009/0225932 A1 | 9/2009 | Zhu et al. |
| 2009/0283682 A1 | 11/2009 | Star-Lack et al. |
| 2010/0046819 A1 | 2/2010 | Noo et al. |
| 2010/0142791 A1 | 6/2010 | Tsuji |
| 2010/0208964 A1 | 8/2010 | Wiegert et al. |
| 2011/0060566 A1 | 3/2011 | Bertram et al. |
| 2011/0142312 A1 | 6/2011 | Toth et al. |
| 2011/0176717 A1 | 7/2011 | Siren et al. |
| 2011/0255657 A1 | 10/2011 | Noordhoek |
| 2012/0014582 A1 | 1/2012 | Schaefer et al. |
| 2012/0121157 A1 | 5/2012 | Irie et al. |
| 2012/0207370 A1 | 8/2012 | Fahimian et al. |
| 2012/0263360 A1 | 10/2012 | Zhu et al. |
| 2012/0294504 A1 | 11/2012 | Kyriakou |
| 2013/0004052 A1 | 1/2013 | Chen et al. |
| 2013/0101082 A1 | 4/2013 | Jordan et al. |
| 2013/0294570 A1 | 11/2013 | Hansis |
| 2014/0018671 A1 | 1/2014 | Li et al. |
| 2014/0086383 A1 | 3/2014 | Huwer et al. |
| 2014/0105352 A1 | 4/2014 | Williams |
| 2014/0110594 A1 | 4/2014 | Star-Lack et al. |
| 2015/0297165 A1 | 10/2015 | Tanaka et al. |
| 2015/0305696 A1 | 10/2015 | Yamakawa et al. |
| 2016/0005194 A1* | 1/2016 | Schretter ............. A61B 6/4233 378/4 |
| 2016/0016009 A1 | 1/2016 | Manzke et al. |
| 2016/0120486 A1 | 5/2016 | Goto et al. |
| 2016/0262709 A1 | 9/2016 | Siewerdsen et al. |
| 2017/0000428 A1 | 1/2017 | Goto |
| 2017/0197098 A1 | 7/2017 | Hirasawa et al. |
| 2017/0205360 A1 | 7/2017 | Cinquin et al. |
| 2017/0278277 A1 | 9/2017 | Morf et al. |
| 2017/0332982 A1 | 11/2017 | Koehler et al. |
| 2018/0028143 A1 | 2/2018 | Wiggers et al. |
| 2018/0070894 A1 | 3/2018 | Osaki et al. |
| 2018/0144510 A1 | 5/2018 | Lachaine |
| 2018/0192978 A1 | 7/2018 | Naylor et al. |
| 2018/0345042 A1 | 12/2018 | Voronenko et al. |
| 2020/0121267 A1 | 4/2020 | Deutschmann |
| 2020/0170590 A1* | 6/2020 | Gagnon ................. A61B 6/488 |
| 2020/0175733 A1* | 6/2020 | Yu ........................... A61B 6/50 |
| 2021/0165122 A1 | 6/2021 | Morton |

FOREIGN PATENT DOCUMENTS

| | | |
|---|---|---|
| EP | 2383702 A1 | 11/2011 |
| JP | H08252248 A | 10/1996 |
| JP | H09218939 A | 8/1997 |
| JP | H105210 A | 1/1998 |
| JP | 2004136021 A | 5/2004 |
| JP | 2005080919 A | 5/2004 |
| JP | 2004530467 A | 10/2004 |
| JP | 2006141999 A | 6/2006 |
| JP | 2006239003 A | 9/2006 |
| JP | 2008036275 A | 2/2008 |
| JP | 2011067555 A | 4/2011 |
| JP | 2012024145 A | 2/2012 |
| JP | 2014511186 A | 5/2014 |
| JP | 2014528767 A | 10/2014 |
| JP | 2017531228 A | 10/2017 |
| WO | 2005112753 A2 | 12/2005 |
| WO | 2006078386 A2 | 7/2006 |
| WO | 2010014288 A1 | 2/2010 |
| WO | 2010099621 A1 | 9/2010 |
| WO | 2015103184 A1 | 7/2015 |
| WO | 2017104700 A1 | 6/2017 |
| WO | 2018156968 A1 | 8/2018 |
| WO | 2018183748 A1 | 10/2018 |

OTHER PUBLICATIONS

Wang, Ge, X-Ray micro-CT with a displaced detector array, Medical Physics, Jul. 2002, pp. 1634-1636, vol. 29, No. 7.

Yu, et al., Radiation dose reduction in computed tomography: techniques and future perspective, Imaging Med., Oct. 2009, pp. 65-84, vol. 1.

Zamyatin, et al., Helical cone beam CT with an asymmetrical detector, Medical Physics, Oct. 2005, pp. 3117-3127, vol. 32, No. 10.

Zbijewski, et al., Efficient Monte Carlo Based Scatter Artifact Reduction in Cone-Beam Micro-CT, IEEE Transactions on Medical Imaging, Jul. 2006, pp. 817-827, vol. 25, No. 7.

Zhu, et al., Scatter Correction Method for X-ray CT Using Primary Modulation: Theory and Preliminary Results, IEEE Transactions on Medical Imaging, Dec. 2006, pp. 1573-1587, vol. 25, No. 12.

Anas, et al., High-quality 3D correction of ring and radiant artifacts in flat panel detector-based cone beam volume CT imaging, Phys. Med. Biol., 2011, pp. 6495-6519, vol. 56.

Bootsma, et al., Spatial frequency spectrum of the x-ray scatter distribution in CBCT projections, Med. Phys., Nov. 2013, pp. 111901-1-111901-15, vol. 40, No. 11.

International Search Report and Written Opinion from PCT/US2021/039824 dated Mar. 4, 2022.

International Search Report and Written Opinion from PCT/US2021/042906 dated Mar. 21, 2022.

Rührnschopf, et al., A general framework and review of scatter correction methods in cone beam CT. Part 2: Scatter estimation approaches, Med. Phys. Sep. 2011, pp. 5186-5199, vol. 38, No. 9.

Yang, et al., Scattering estimation for cone-Beam CT Using Local Measurement Based on Compressed Sensing, IEEE transactions on Nuclear Science, Mar. 2018, pp. 941-949, vol. 65, No. 3.

Clackdoyle, et al., Data consistency conditions for truncated fanbeam and parallel projections, Med. Phys. Feb. 2015, pp. 831-845, vol. 42, No. 2.

Defrise, et al., A solution to the long-object problem in helical cone-beam tomography, Physics in Medicine and Biology, 2000, pp. 623-643, vol. 45.

Hsieh, et al., A novel reconstruction algorithm to extend the CT scan field-of-view, Med. Phys., Sep. 2004, pp. 2385-2391, vol. 31, No. 9.

International Search Report and Written Opinion from PCT/US2019/063071 dated Mar. 18, 2020.

International Search Report and Written Opinion from PCT/US2019/063073 dated Apr. 3, 2020.

International Search Report and Written Opinion from PCT/US2019/063074 dated Mar. 23, 2020.

International Search Report and Written Opinion from PCT/US2019/063076 dated Mar. 16, 2020.

International Search Report and Written Opinion from PCT/US2019/063077 dated Mar. 16, 2020.

International Search Report and Written Opinion from PCT/US2019/063078 dated Oct. 8, 2020.

International Search Report and Written Opinion from PCT/US2019/063080 dated Mar. 16, 2020.

International Search Report and Written Opinion from PCT/US2019/063083 dated Mar. 16, 2020.

International Search Report and Written Opinion from PCT/US2019/063085 dated Mar. 16, 2020.

(56) References Cited

OTHER PUBLICATIONS

International Search Report and Written Opinion from PCT/US2019/063086 dated Nov. 16, 2020.
International Search Report and Written Opinion from PCT/US2019/063087 dated Apr. 3, 2020.
Invitation to Pay Additional Fees from PCT/US2019/063086 dated Mar. 26, 2020.
Kang et al., Accurate positioning for head and neck cancer patients using 2D and 3D image guidance, Journal of Applied Clinical Medical Physics, Mar. 2011, pp. 1-14, vol. 12, No. 1.
Katsevich, A., An improved exact filtered backprojection algorithm for spiral computed tomography, Advances in Applied Mathematics, 2004, pp. 691-697, vol. 32.
Kudo et al., Exact and approximate algorithms for helical cone-beam CT, Physics in Medicine and Biology, 2004, pp. 1-26, vol. 49, No. 13.
Kunze, et al., Cone beam reconstruction with displaced flat panel detector, 10th International Meeting on Fully Three-Dimensional Image Reconstruction in Radiology and Nuclear Medicine, 2009, pp. 138-141.
Li et al., Scatter kernel estimation with an edge-spread function method for cone-beam computed tomography imaging. Physics in Medicine and Biology, pp. 6729-6748, vol. 51.
Liu et al., X-Ray micro-CT with a displaced detector array: Application to helical cone-beam reconstruction, Medical Physics, Oct. 2003, pp. 2758-2761, vol. 30, No. 10.
Maslowski, et al., Acuros CTS: A fast, linear Boltzmann transport equation solver for computed tomography scatter-Part I: Core algorithms and validation, Med. Phys., 2018, pp. 1-15.
Ning, et al., X-ray scatter correction algorithm for cone beam CT imaging, Med. Phys., May 2004, pp. 1195-1202, vol. 31, No. 5.
Noo et al., A new scheme for view-dependent data differentiation in fan-beam and cone-beam computed tomography, Physics in Medicine and Biology, 2007, pp. 5593-5414, vol. 52.
Notice of Allowance from U.S. Appl. No. 16/694,190 dated Jun. 23, 2021, 8 pages.
Office Action from U.S. Appl. No. 16/694,202 dated Apr. 9, 2021, 12 pages.
Office Action from U.S. Appl. No. 16/694,145 dated Mar. 17, 2021, 10 pages.
Office Action from U.S. Appl. No. 16/694,190 dated Mar. 26, 2021, 9 pages.
Office Action from U.S. Appl. No. 16/694,192 dated Jun. 10, 2021, 10 pages.
Office Action from U.S. Appl. No. 16/694,218 dated Apr. 15, 2021, 7 pages.
Office Action from U.S. Appl. No. 16/694,230 dated Apr. 1, 2021, 6 pages.
Ramamurthi et al., Region of Interest Cone Beam Tomography With Prior CT Data, Conference Record of the 37th Asilomar Conference on Signals, Systems, & Computers, Nov. 2003, pp. 1924-1927, vol. 2.
Restriction Requirement from U.S. Appl. No. 16/694,210 dated Jun. 10, 2021, 6 pages.
Schäfer, et al., Cone-beam filtered back-projection for circular X-ray tomography with off-center detector, 10th International Meeting on Fully Three-Dimensional Image Reconstruction in Radiology and Nuclear Medicine, 2009, pp. 86-89.
Schäfer, et al., FBP and BPF reconstruction methods for circular X-ray tomography with off-center detector, Med. Phys., Jul. 2011, pp. S85-S94, vol. 38, No. 7.
Siewerdsen, et al., A simple, direct method for x-ray scatter estimation and correction in digital radiography and cone-beam CT, Med. Phys., Jan. 2006, pp. 187-197, vol. 33, No. 1.
Spearman, et al., Effect of Automated Attenuation-based Tube Voltage Selection on Radiation Dose at CT: An Observational Study on a Global Scale, Radiology, Apr. 2016, pp. 167-174, vol. 279, No. 1.
Sun, et al., Improved scatter correction using adaptive scatter kernel superposition, Physics in Medicine and Biology, Oct. 2010, pp. 6695-6720, vol. 55.
Fang, et al., A sinogram extrapolation method for CT field of view extension, Proceedings of the Fifth CT Meeting, 2018, pp. 206-209.
Office Action from U.S. Appl. No. 16/694,161 dated Sep. 13, 2021, 18 pages.
Invitation to Pay Additional Fees from PCT/US2022/035500 dated Oct. 13, 2022, 14 pages.
Notice of Allowance from U.S. Appl. No. 17/383,740 dated Mar. 15, 2023, 11 pages.
European Search Report from EP 23155102.9 dated Jul. 4, 2023.
Office Action from European Application No. 19824059.0 dated Jul. 18, 2023, 4 pages.
Office Action from European Application No. 19824061.6 dated Jul. 24, 2023, 4 pages.
Office Action from Japanese Application No. 2021-531086 dated Jul. 11, 2023, 3 pages.
Office Action from Japanese Application No. 2021-531085 dated Jul. 25, 2023, 8 pages.
Office Action from Japanese Application No. 2021-531084 dated Jul. 25, 2023, 8 pages.
Office Action from Japanese Application No. 2021-521836 dated Aug. 15, 2023, 19 pages.
Office Action from Japanese Application No. 2021-521751 dated Aug. 29, 2023, 5 pages.
Office Action from Japanese Application No. 2021-521845 dated Aug. 29, 2023, 4 pages.

\* cited by examiner

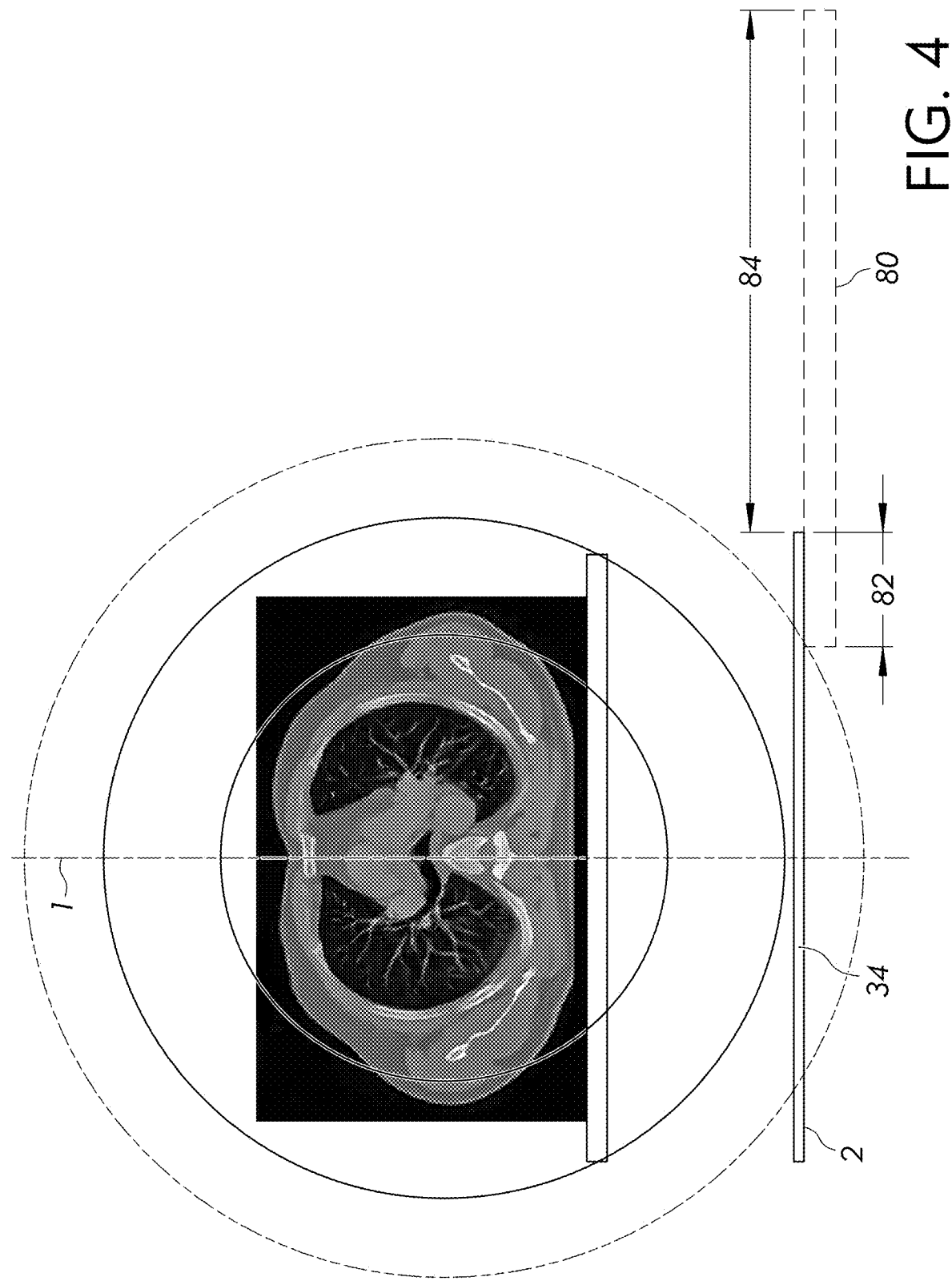

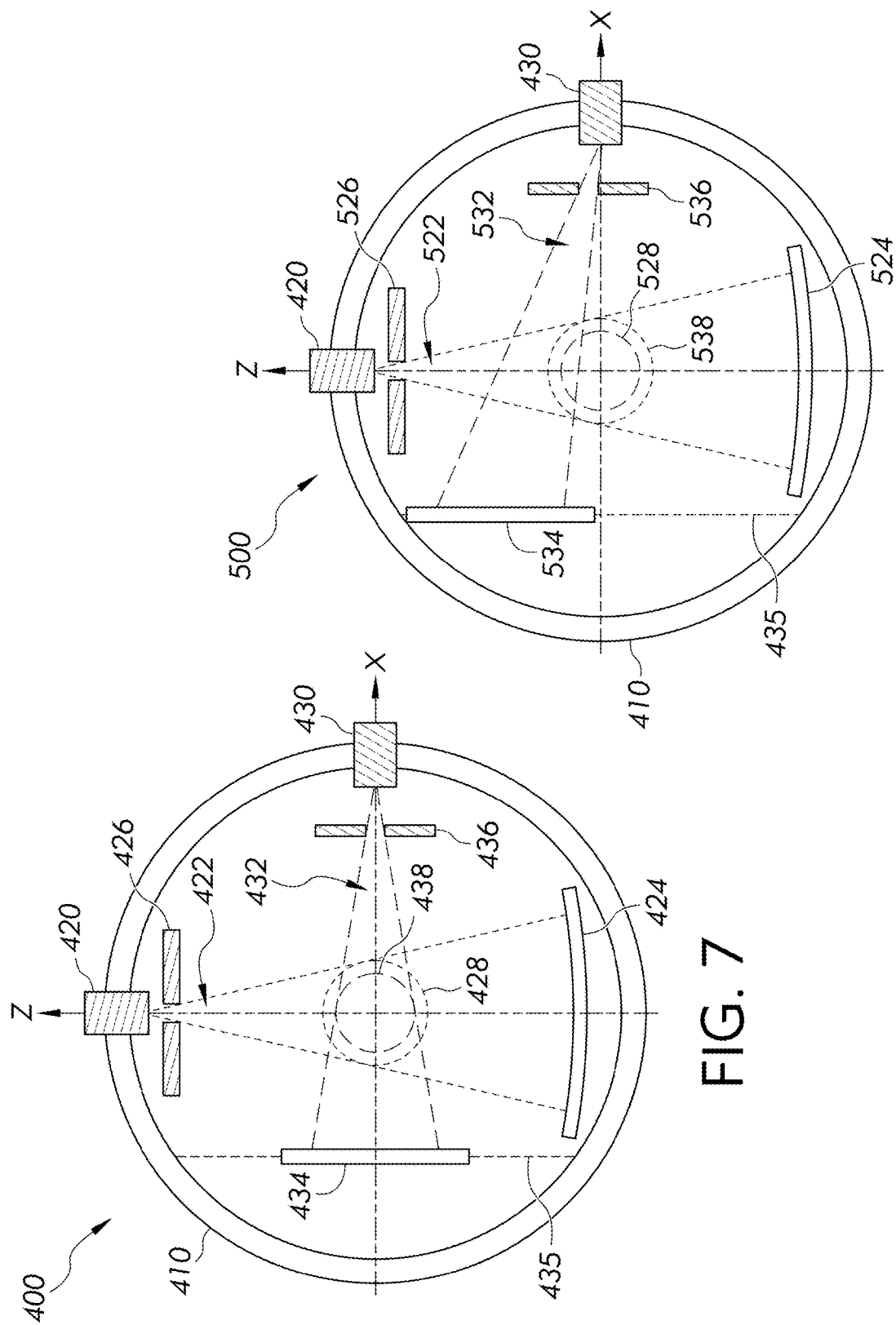

MULTIMODAL RADIATION APPARATUS AND METHODS

FIELD OF THE INVENTION

This disclosure relates to utilizing multimodal radiation for imaging, and, more particularly, utilizing low-energy radiation (e.g., kilovolt (kV)) and high-energy radiation (e.g., megavolt (MV)) in combination for improved imaging, including for computed tomography (CT) scans.

BACKGROUND

The term "radiosurgery" refers to a procedure in which radiation is applied to a target region at doses sufficient to necrotize a pathology in fewer treatment sessions or fractions than with delivery of lower doses per fraction in a larger number of fractions. Radiosurgery is typically characterized, as distinguished from radiotherapy, by relatively high radiation doses per fraction (e.g., 500-2000 centigray) and hypo-fractionation (e.g., one to five fractions or treatment days). Radiotherapy is typically characterized by a low dose per fraction (e.g., 100-200 centigray) and hyper-fractionation (e.g., 30 to 45 fractions). For convenience, the terms "radiation treatment" and "radiation therapy" are used interchangeably herein to mean radiosurgery and/or radiotherapy unless otherwise noted.

Associated with each radiation therapy system is an imaging system to provide images that are used to set up and, in some examples, guide the radiation delivery procedure and track in-treatment target motion. Known approaches utilize distinct, independent image radiation source(s) and/or detector(s) for the patient set-up and in-treatment images. Target or target volume tracking during treatment is accomplished by comparing in-treatment images to prior or pre-treatment image information. Pre-treatment image information may comprise, for example, CT data, cone-beam CT (CBCT) data, magnetic resonance imaging (MRI) data, positron emission tomography (PET) data or 3D rotational angiography (3DRA) data, and any information obtained from these imaging modalities (for example and without limitation, digitally reconstructed radiographs (DRRs)).

There are typically two general goals in radiation therapy: (i) to deliver a highly conformal dose distribution to the target volume (by utilizing CT imaging to conform the delivery/dose of radiation to the shape of the target; normal tissue is spared as much as possible); and (ii) to deliver treatment beams with high accuracy throughout every treatment fraction. A third goal is to accomplish the two general goals in as little time per fraction as possible. Delivering a more conformal dose distribution may require, for example, the ability to deliver non-coplanar beams. Delivering treatment beams accurately may require the ability to track the location of the target volume intrafraction. The ability to increase delivery speed requires the ability to accurately, precisely, and quickly move the radiation source without hitting other objects in the room or the patient, and/or violating regulatory agency speed limitations.

CBCT has been proposed as an in-treatment imaging modality for use in conjunction with radiation treatment systems, in some cases as a kV imaging modality and in other cases as a MV (portal) imaging modality. CBCT imaging directly constructs a 3D volumetric image from 2D projections of the target volume and CBCT offers the ability to form a 3D image volume from a single gantry rotation (more specifically, a rotation of at least 180 degrees plus a fan beam angle) about the target volume. CBCT also provides for a more isotropic spatial resolution.

Dose calculation and treatment planning using CBCT requires that the CBCT images be of high quality and quantitative accuracy. However, when lateral, in-plane patient truncation (i.e., transaxial truncation) occurs, artifacts and quantitative bias are introduced, making the CBCT image possibly unsuitable for use in dose calculation and treatment planning. Although transaxial patient truncation can be reduced by patient positioning and scanning field-of-view (FOV) selection, automatic patient positioning and FOV selection may be challenging. For example, selection of a FOV that is smaller than the patient size and/or off-centered patient positioning within the FOV may result in lateral (i.e., transaxial) truncation. Additionally, selection of a FOV that is larger than sufficient requires a greater detector offset, a greater detector area unused to detect patient data, and less useful patient data for the same patient dose.

Conventional CBCT systems using flat-panel detectors offset the flat-panel laterally relative to a center beam 1 by moving the flat-panel detector from a first position 2 to a second position 3, to achieve an enlarged effective FOV 4 compared to original FOV 5, as shown in FIG. 1. However, the offset is limited to half of the lateral dimension of the detector, less a minimal overlap region 6. For example, if the lateral dimension of the detector is 40 cm and an overlap is 5 cm, then the maximum offset 7 of the detector is 15 cm. The effective maximum scanning FOV 4 is equivalent to that of a virtual centered detector with a dimension that is the sum of the actual detector lateral dimension plus twice the maximum offset 7, or 70 cm for the previous example.

Accordingly, there may be a need for alternative systems and methods for reducing transaxial patient truncation and increasing a maximum FOV size. Various embodiments described herein can enable the effective scanning FOV of a CBCT system to surpass the conventional limit and/or automatic FOV selection for patient scans while reducing or even avoiding transaxial patient truncation.

BRIEF SUMMARY

In a first embodiment, an imaging apparatus comprises a rotatable gantry system positioned at least partially around a patient support; a first source of radiation coupled to the rotatable gantry system, the first source of radiation configured for imaging radiation; a second source of radiation coupled to the rotatable gantry system; and a first radiation detector coupled to the rotatable gantry system and laterally movable relative to a central beam of the first source of radiation to receive radiation from at least the first source of radiation over various fields of view.

According to a second embodiment, an imaging apparatus comprises the imaging apparatus according to the first embodiment, wherein first scan data is acquired during a first scan, second scan data is acquired during a second scan, and the first scan data and the second scan data are combined to provide a dataset corresponding to an effective field of view of the imaging apparatus that is greater than any of the various fields of view individually.

According to a third embodiment, an imaging apparatus comprises the imaging apparatus according to the second embodiment, wherein the first radiation detector is in the first position during the first scan, the first radiation detector is in the second position during the second scan, and the first position and the second position have a lateral overlap.

According to a fourth embodiment, an imaging apparatus comprises the imaging apparatus according to the second or third embodiments, and further comprises a reconstruction processor configured to generate a reconstructed image based on a dataset comprising the first scan data and the second scan data, wherein the dataset has reduced transaxial truncation as compared to each of the first scan data and the second scan data.

According to a fifth embodiment, an imaging apparatus comprises the imaging apparatus according to any one of the second through fourth embodiments, the first scan comprising a first helical scan, the second scan comprising a second helical scan, wherein the patient support moves in the second scan relative to the first scan in the transaxial plane.

According to a sixth embodiment, an imaging apparatus comprises the imaging apparatus according to any preceding embodiment, wherein at least one of the first source of radiation or the second source of radiation is configured to produce a cone beam geometry.

According to a seventh embodiment, an imaging apparatus comprises the imaging apparatus according to any preceding embodiment, wherein the second source of radiation is configured as a source of therapeutic radiation.

According to an eighth embodiment, an imaging apparatus comprises a gantry system rotatable about a central axis; a source of radiation coupled to the gantry system; and a radiation detector coupled to the rotatable gantry system and laterally movable between a first position in which the radiation detector interacts with a central beam of the source of radiation, and a second position in which the radiation detector does not interact with the central beam of the source of radiation, wherein the first position and the second position have lateral overlap.

According to a ninth embodiment, an imaging apparatus comprises the imaging apparatus according to the eighth embodiment, wherein first scan data is acquired during a first scan with the detector at the first position, second scan data is acquired during a second scan with the detector at the second position, and the first scan data and the second scan data are combined to provide a dataset corresponding to an effective field of view of the imaging apparatus that is greater than any of the various fields of view individually.

According to a tenth embodiment, an imaging apparatus comprises the imaging apparatus according to the eighth or ninth embodiments, and further comprising a reconstruction processor configured to generate a reconstructed image based on a dataset comprising first scan data acquired during a first scan with the detector at the first position and second scan data acquired during a second scan with the detector at the second position, wherein the dataset has reduced transaxial truncation as compared to the first scan data and the second scan data or no transaxial truncation.

According to an eleventh embodiment, an imaging apparatus comprises the imaging apparatus of any of the eighth through tenth embodiments, wherein the source of radiation is configured to produce a cone beam geometry.

According to a twelfth embodiment, an imaging apparatus comprises the imaging apparatus of any of the eighth through eleventh embodiments, wherein the source of radiation is a first source of radiation, and wherein the imaging apparatus further comprises a second source of radiation, the second source of radiation being configured as a source of therapeutic radiation.

According to a thirteenth embodiment, an imaging apparatus comprises the imaging apparatus of the twelfth embodiment, wherein the second source of radiation has an energy level the same as or greater than the first source of radiation.

According to a fourteenth embodiment, an imaging apparatus comprises the imaging apparatus of any of the twelfth or thirteenth embodiments, wherein the radiation detector comprises a flat panel radiation detector.

According to a fifteenth embodiment, a method of using an imaging apparatus comprises: receiving data corresponding to an image of a patient positioned on a patient support; receiving first scan data from a source of radiation at a radiation detector, the source of radiation configured for imaging radiation, wherein the first scan data comprises a scan field of view (FOV) and the first scan data is acquired during a first scan while the radiation detector is in a first position relative to a central beam of the source of radiation and the patient support is in a first position relative to a central axis of a rotatable gantry system that at least partially surrounds the patient support; selecting an effective FOV based on the received data corresponding to the image and the first scan data, wherein the effective FOV is selected to minimize transaxial truncation in a projection of the patient; and determining a second position of at least one of the radiation detector relative to the central beam of the source of radiation and the patient support with respect to the central axis of the rotatable gantry system based on the selected effective FOV, wherein the second position is laterally offset from the first position.

According to a sixteenth embodiment, a method comprises the method of the fifteenth embodiment, and further comprises receiving second scan data from the source of radiation at the radiation detector, the second scan data being acquired during a second scan while the at least one of the radiation detector and the patient support is in the second position.

According to a seventeenth embodiment, a method comprises the method of the sixteenth embodiment and further comprises generating a reconstructed image based on a dataset comprising the first scan data and the second scan data, wherein the dataset is within the effective FOV and has reduced transaxial truncation as compared to the first scan data and the second scan data or has no transaxial truncation.

According to an eighteenth embodiment, a method comprises the method of the sixteenth or seventeenth embodiments, the first scan comprising a first helical scan, the second scan comprising a second helical scan, wherein the patient support moves in first longitudinal direction relative to the rotatable gantry system during the first helical scan, and in a second longitudinal direction relative to the rotatable gantry system during the second helical scan, the second longitudinal direction being opposite the first longitudinal direction.

According to a nineteenth embodiment, a method comprises the method of any one of the sixteenth through eighteenth embodiments, wherein the first scan data is acquired during the first scan while the radiation detector is in the first position and the second scan data is acquired during the second scan while the radiation detector is in the second position.

According to a twentieth embodiment, a method comprises the method of any one of the sixteenth through nineteenth embodiments, wherein the first scan data is acquired during the first scan while the patient support is in the first position and the second scan data is acquired during the second scan while the patient support is in the second position.

Features that are described and/or illustrated with respect to one embodiment may be used in the same way or in a similar way in one or more other embodiments and/or in combination with or instead of the features of the other embodiments.

The descriptions of the invention do not limit the words used in the claims in any way or the scope of the claims or invention. The words used in the claims have all of their full ordinary meanings.

BRIEF DESCRIPTION OF THE DRAWINGS

In the accompanying drawings, which are incorporated in and constitute a part of the specification, embodiments of the invention are illustrated, which, together with a general description of the invention given above, and the detailed description given below, serve to exemplify embodiments of this invention. It will be appreciated that illustrated element boundaries (e.g., boxes, groups of boxes, or other shapes) in the figures represent one embodiment of boundaries. In some embodiments, one element may be designed as multiple elements or that multiple elements may be designed as one element. In some embodiments, an element shown as an internal component of another element may be implemented as an external component and vice versa. Furthermore, elements may not be drawn to scale.

FIG. 4 is a diagrammatic illustration of a detector configuration in accordance with one or more embodiments described herein.

FIG. 7 shows an illustration of an exemplary multimodal scan configuration in accordance with one or more embodiments described herein.

FIG. 8 shows an illustration of another exemplary multimodal scan configuration in accordance with one or more embodiments described herein.

DETAILED DESCRIPTION

Figure 1:
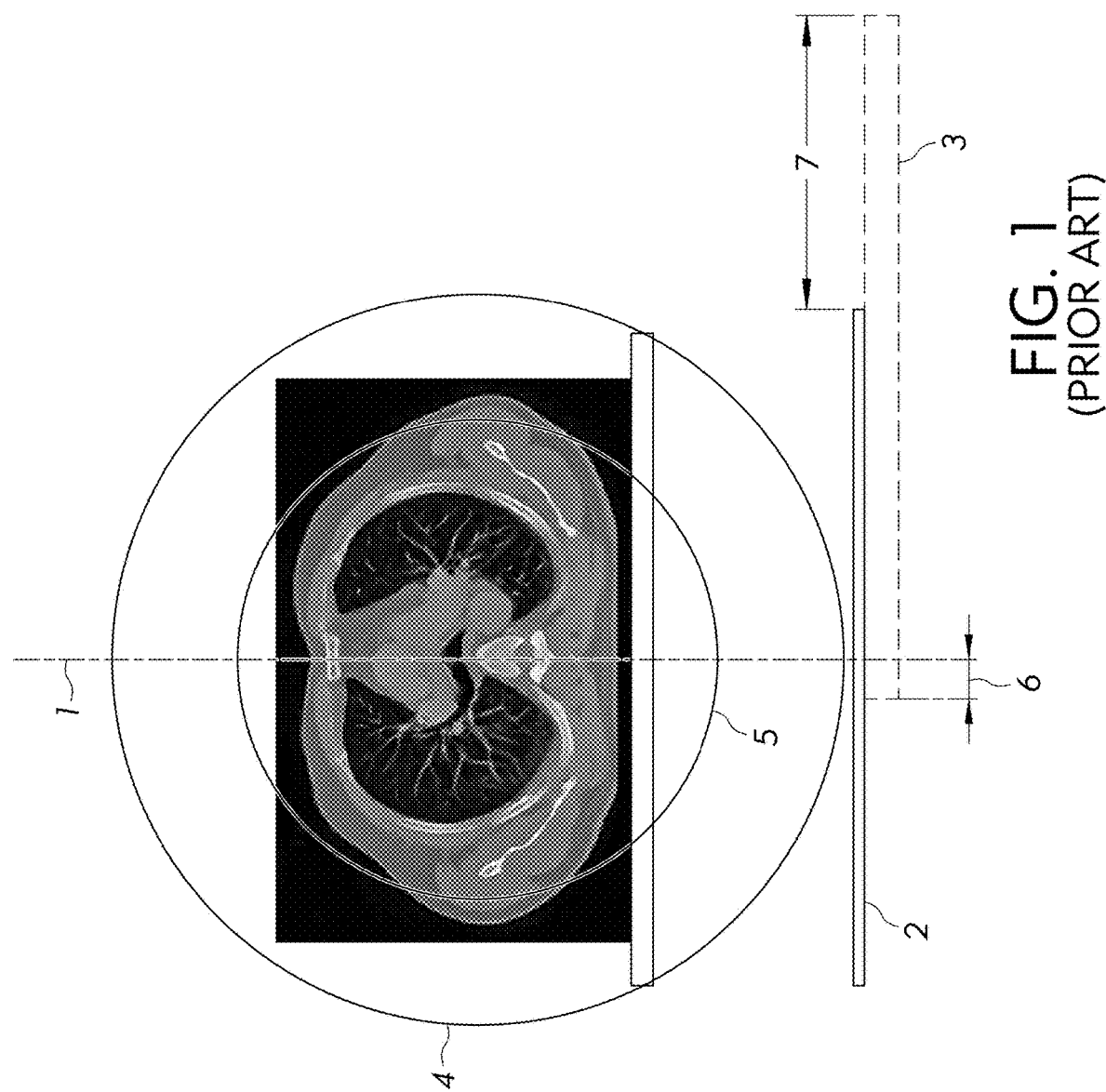
FIG. 1 is a diagrammatic illustration of a prior art offset detector configuration.

The following includes definitions of exemplary terms that may be used throughout the disclosure. Both singular and plural forms of all terms fall within each meaning.

"Component," as used herein can be defined as a portion of hardware, a portion of software, or a combination thereof. A portion of hardware can include at least a processor and a portion of memory, wherein the memory includes an instruction to execute. A component may be associated with a device.

"Logic," synonymous with "circuit" as used herein, includes but is not limited to hardware, firmware, software and/or combinations of each to perform a function(s) or an action(s). For example, based on a desired application or needs, logic may include a software-controlled microprocessor, discrete logic such as an application specific integrated circuit (ASIC), or other programmed logic device and/or controller. Logic may also be fully embodied as software.

"Processor," as used herein includes, but is not limited to, one or more of virtually any number of processor systems or stand-alone processors, such as microprocessors, microcontrollers, central processing units (CPUs), and digital signal processors (DSPs), in any combination. The processor may be associated with various other circuits that support operation of the processor, such as random access memory (RAM), read-only memory (ROM), programmable read-only memory (PROM), erasable programmable read-only memory (EPROM), clocks, decoders, memory controllers, or interrupt controllers, etc. These support circuits may be internal or external to the processor or its associated electronic packaging. The support circuits are in operative communication with the processor. The support circuits are not necessarily shown separate from the processor in block diagrams or other drawings.

"Signal," as used herein includes, but is not limited to, one or more electrical signals, including analog or digital signals, one or more computer instructions, a bit or bit stream, or the like.

"Software", as used herein, includes but is not limited to one or more computer readable and/or executable instructions that cause a computer, processor, logic, and/or other electronic device to perform functions, actions, and/or behave in a desired manner. The instructions may be embodied in various forms such as routines, algorithms, modules, or programs including separate applications or code from dynamically linked sources or libraries.

While the above exemplary definitions have been provided, it is Applicant's intention that the broadest reasonable interpretation consistent with this specification be used for these and other terms.

As is discussed in more detail below, embodiments of the disclosed technology relate to multimodal imaging/radiotherapy devices and methods that employ dual scans to enable an increased effective scanning FOV as compared to a conventional CBCT system and/or enable automatic FOV selection for patient scans while reducing or avoiding transaxial patient truncation. In various embodiments, a detector of the multimodal imaging/radiotherapy device is in a first position for a first scan, and is moved to a second position for a second scan. Data obtained from the first scan and the second scan is combined to provide a dataset with reduced transaxial truncation (e.g., as compared to each of the first scan data or the second scan data alone) or even without transaxial truncation, thereby enabling the resultant image to be used for dose calculation and treatment planning.

Although described in various embodiments as a "dual scan" or "first scan" and "second scan", the image acquisition methodology can include or otherwise make use of a multiple rotation scan, which may be, for example, a continuous scan (e.g., with a helical source trajectory about a central axis together with longitudinal movement of a patient support through a gantry bore), a non-continuous circular stop-and-reverse scan with incremental longitudinal movement of a patient support, step-and-shoot circular scans, etc. Accordingly, the phrase "dual scan," as used herein, refers to scans including multiple rotations, which may be continuous or non-continuous.

Figure 2:
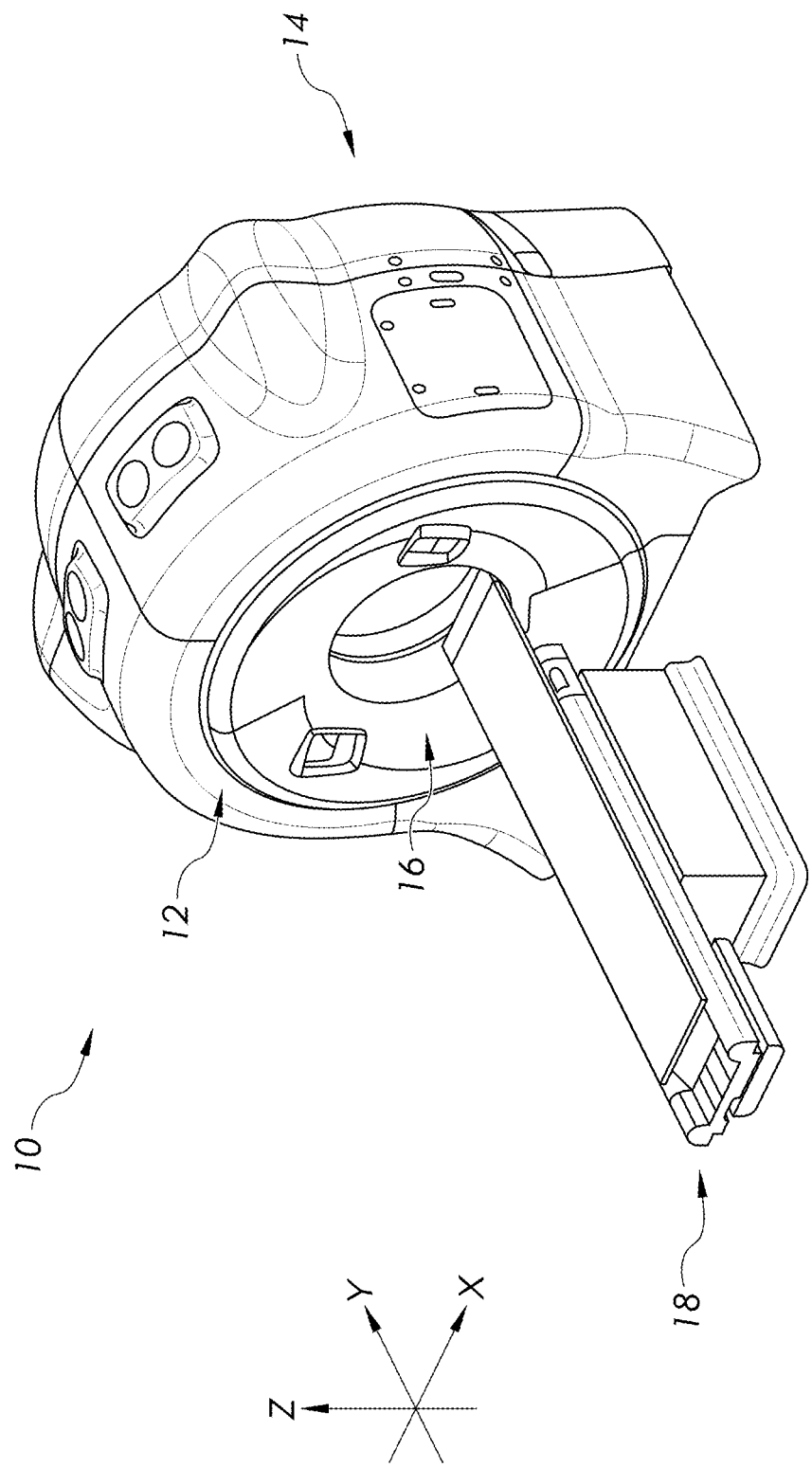
FIG. 2 is a perspective view of an exemplary multimodal radiotherapy apparatus in accordance with one or more embodiments described herein.
Figure 3:
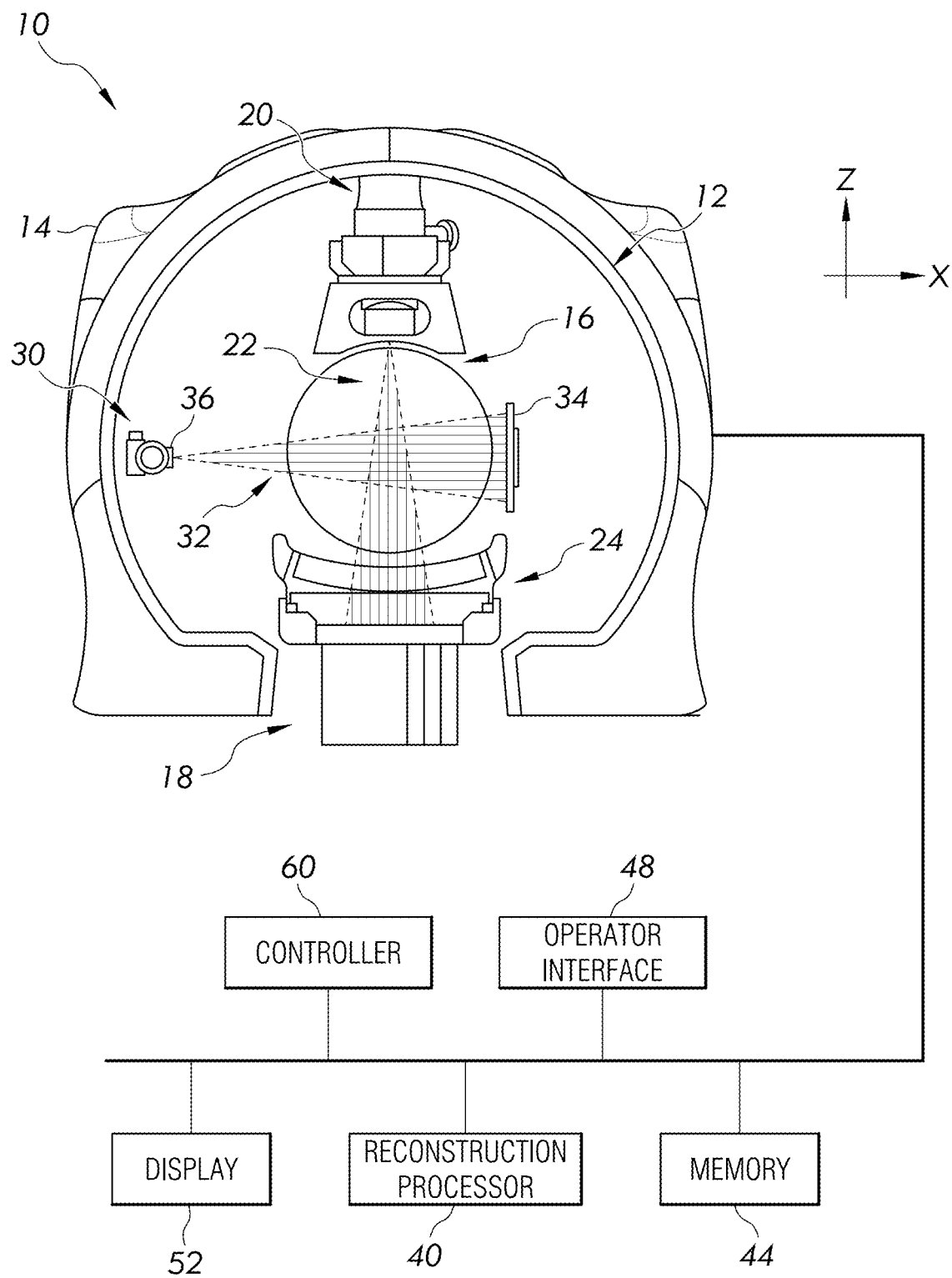
FIG. 3 is a diagrammatic illustration of an exemplary multimodal radiotherapy device in accordance with one or more embodiments described herein.

With reference to FIG. 2 and FIG. 3, a multimodal apparatus 10 is shown. It will be appreciated that the multimodal apparatus 10 may be associated with and/or integrated into a radiotherapy device (as shown in FIG. 3) that can be used for a variety of applications, including, but not limited to IGRT, for example, as an IGRT delivery system (e.g., IGRT delivery system 104 shown in FIG. 5 and discussed in detail below). The multimodal apparatus 10 includes a rotatable gantry system, referred to as gantry 12, supported by or otherwise housed in a support unit or housing 14. Gantry herein refers to a gantry system that comprises one or more gantries (e.g., ring or C-arm) capable of supporting one or more radiation sources and/or associated detectors as they rotate around a target. For example, in one embodiment, a first radiation source and its associated detector may be mounted to a first gantry of the gantry system and a second radiation source and its associated detector may be mounted to a second gantry of the gantry system. In another embodiment, more than one radiation source and associated detector(s) may be mounted to the same gantry of the gantry system, including, for example, where the gantry system is comprised of only one gantry. Various combinations of gantries, radiation sources, and radiation detectors may be combined into a variety of gantry system configurations to image and/or treat the same volume within the same apparatus. For example, kV and MV radiation sources can be mounted on the same or different gantries of the gantry system and selectively used for imaging and/or treatment as part of an IGRT system. If mounted to different gantries, the radiation sources are able to rotate independently, but are still able to simultaneously image the same (or nearly the same) volume. A rotatable ring gantry 12 may be capable of 10 rpm or more.

The rotatable gantry 12 defines a gantry bore 16 into and through which a patient can be moved and positioned for imaging and/or treatment. In accordance with one embodiment, the rotatable gantry 12 is configured as a slip ring gantry to provide continuous rotation of radiation sources and associated radiation detector(s) while providing sufficient bandwidth for the high-quality imaging data received by the detector(s). A slip-ring gantry can eliminate gantry rotations in alternating directions in order to wind and unwind cables carrying the power and signals associated with the device. Such a configuration will allow for continuous helical computed tomography, including CBCT, even when integrated into an IGRT system.

A patient support 18 is positioned adjacent to the rotatable gantry 12 and configured to support a patient, typically in a horizontal position, for longitudinal movement into and within the rotatable gantry 12. The patient support 18 can move the patient, for example, in a direction perpendicular to the plane of rotation of the gantry 12 (along or parallel to the rotation axis of the gantry 12). The patient support 18 can be operatively coupled to a patient support controller for controlling movement of the patient and patient support 18. The patient support controller can be synchronized with the rotatable gantry 12 and sources of radiation mounted to the rotating gantry for rotation about a patient longitudinal axis in accordance with a commanded imaging and/or treatment plan. The patient support can also be moved in a limited range up and down, left and right once it is in the bore 16 to adjust the patient position for optimal treatment. Axes x, y, and z are shown, where, viewing from the front of the gantry 12, the x-axis is horizontal and points to the right, the y-axis points into the gantry plane, and the z-axis is vertical and points to the top. The x-, y-, and z-axes follow the right-hand rule.

As shown in FIG. 3, the multimodal apparatus 10 includes a low-energy radiation source (e.g., kV) 30 coupled to or otherwise supported by the rotatable gantry 12. In this embodiment, the low-energy radiation source 30 is a source of imaging radiation and emits a radiation beam (indicated generally as 32) for generating high-quality images. In this embodiment, the source of imaging radiation is an x-ray source 30, configured as a kilovoltage (kV) source (e.g., a clinical x-ray source having an energy level in the range of about 20 kV to about 150 kV). In one embodiment, the low energy radiation source comprises a kilo-electron volt peak photon energy (keV) up to 150 keV. The imaging radiation source can be any type of transmission source suitable for imaging. For example, the imaging radiation source may be, for example, an x-ray generating source (including for CT) or any other way to produce photons with sufficient energy and flux (such as, e.g., a gamma-source (e.g., Cobalt-57, energy peak at 122 keV), an x-ray fluorescence source (such as fluorescence source through Pb k lines, two peaks at about 70 keV and at about 82 keV), etc.). References herein to x-ray, x-ray imaging, x-ray imaging source, etc. are exemplary for particular embodiments. Other imaging transmission sources can be used interchangeably in various other embodiments. An x-ray detector 34 (e.g., two-dimensional flat detector) can be coupled to or otherwise supported by the rotatable gantry 12. The x-ray detector 34 is positioned to receive radiation from the x-ray source 30 and can rotate along with the x-ray source 30.

It will be appreciated that the x-ray detector 34 can take on a number of configurations without departing from the scope of the disclosed technology. As illustrated in FIGS. 3 and 4, the x-ray detector 34 can be configured as a flat-panel detector (e.g., a multi-row flat panel detector). The detector 34 can detect or otherwise measure the amount of radiation not attenuated and therefore infer what was in fact attenuated by the patient or associated patient ROI (by comparison to what was initially generated). The detector 34 can detect or otherwise collect attenuation data from different angles as the low-energy radiation source 30 rotates around and emits radiation toward the patient.

Although FIGS. 2 and 3 depict a multimodal apparatus 10 with a radiation source 30 mounted to a ring gantry 12, other embodiments may include other types of rotatable imaging apparatuses, including, for example, C-arm gantries and robotic arm-based systems. In gantry-based systems, a gantry rotates the imaging radiation source 30 around an axis passing through the isocenter. Gantry-based systems include C-arm gantries, in which the imaging radiation source 30 is mounted, in a cantilever-like manner, over and rotates about the axis passing through the isocenter. Gantry-based systems further include ring gantries, for example, rotatable gantry 12, having generally toroidal shapes in which the patient's body extends through a bore of the ring/toroid, and the imaging radiation source 30 is mounted on the perimeter of the ring and rotates about the axis passing through the isocenter. In some embodiments, the gantry 12 rotates continuously. In other embodiments, the gantry 12 utilizes a cable-based system that rotates and reverses repeatedly.

A collimator or beamformer assembly (indicated generally as 36) is positioned relative to the x-ray source 30 to selectively control and adjust a shape of a radiation beam 32 emitted by the x-ray source 30 to selectively expose a portion or region of the active area of the x-ray detector 34. The beamformer can also control how the radiation beam 32 is positioned on the x-ray detector 34. In one embodiment, the beamformer 36 could have one degree/dimension of motion (e.g., to make a thinner or fatter slit). In another embodiment, the beamformer 36 can have two degrees/dimensions of motion (e.g., to make various sized rectangles). In other embodiments, the beamformer 36 may be capable of various other dynamically-controlled shapes, including, for example, parallelograms. All of these shapes may be dynamically adjusted during a scan. In some embodiments, blocking portions of the beamformer can be rotated and/or translated.

The beamformer 36 can be controlled to adjust the shape of the radiation beam 32 emitted by the x-ray source 30 dynamically in a number of geometries, including, but not limited to, a fan beam or cone beam having a beam thickness (width) as low as one detector row width or including multiple detector rows, which may be only a portion of the detector's active area. In various embodiments, the thickness of the beam may expose several centimeters of a larger detector active area. For example, from about 3 to about 4 centimeters (measured in the longitudinal direction in the detector plane) of a detector having an active are of from about 5 to about 6 centimeters may be selectively exposed to the imaging radiation 32. In this embodiment, from about 3 to about 4 centimeters of projection image data may be captured with each readout, with from about 1 to about 2 centimeters of unexposed detector area on one or each side, which may be used to capture scatter data, as discussed below.

In other embodiments, more or less of a portion of the active detector may be selectively exposed to the imaging radiation. For example, in some embodiments, the beam thickness may be reduced down to about two centimeters, one centimeter, less than one centimeter, or ranges of similar sizes, including with smaller detectors. In other embodiments, the beam thickness may be increased to about 4 centimeters, about 5 centimeters, greater than 5 centimeters, or ranges of similar sizes, including with larger detectors. In various embodiments, the ratio of exposed-to-active detector area may be from about 30% to about 90% or from about 50% to about 75%. In other embodiments, the ratio of exposed-to-active detector area may be from about 60% to about 70%. However, various other exposed and active area sizes or ratios of exposed-to-active detector area may be suitable in other embodiments. The beam and detector can be configured so that the shadowed region of the detector (active but not exposed to direct radiation) is sufficient to capture scatter data beyond the penumbra region.

Various embodiments may include an optimization of the features that control selective exposure of the detector (e.g., beam size, beam/aperture center, collimation, pitch, detector readout range, detector readout center, etc.) such that the measured data is sufficient for primary (exposed) and shadowed regions, but also optimized for speed and dosage control. The beamformer 36 shape/position and detector 34 readout range can be controlled such that the radiation beam 32 from the x-ray source 30 covers as much or as little of the x-ray detector 34 based on the particular imaging task and scatter estimation process being carried out, including, for example, combinations of narrow and wide axial field-of-view (aFOV) scans, as will be described in greater detail below. The apparatus 10 has the ability to acquire both single rotation cone beam and wide and narrow beam angle images, helical or other.

The beamformer 36 may be configured in a variety of ways that allow it to adjust the shape of the radiation beam 32 emitted by the x-ray source 30. For example, the beamformer 36 can be configured to include a set of jaws or other suitable members that define and selectively adjust the size of an aperture through which the radiation beam from the x-ray source 30 may pass in a collimated manner. In accordance with one exemplary configuration, the beamformer 36 can include an upper jaw and a lower jaw, where the upper and lower jaws are movable in different directions (e.g., parallel directions) to adjust the size of the aperture through which the radiation beam from the x-ray source 30 passes, and also to adjust the beam 32 position relative to the patient to illuminate only the portion of the patient to be imaged for optimized imaging and minimized patient dose.

In accordance with one embodiment, the shape of the radiation beam 32 from the x-ray source 30 can be changed during an image acquisition. Stated differently, in accordance with one exemplary implementation, the beamformer 36 leaf positions and/or aperture width can be adjusted before or during a scan. For example, in accordance with one embodiment, the beamformer 36 can be selectively controlled and dynamically adjusted during rotation of the x-ray source 30 such that the radiation beam 32 has a shape with sufficient primary/shadow regions and is adjusted to include only an object of interest during imaging (e.g., the prostate). The shape of the radiation beam 32 being emitted by the x-ray source 30 can be changed during or after a scan, depending on the desired image acquisition, which may be based on imaging and/or therapeutic feedback, as discussed in more detail below.

As shown in FIG. 4, the detector 34 is movable between a first position 2, in which the detector 34 is centered relative to the center beam 1, and a second position 80 (shown in phantom), in which the detector 34 is offset relative to the center beam 1. In embodiments, the center beam 1 is not captured by the detector 34 in the second position. For example, the detector 34 may be mounted to a detector assembly, which is, in turn, coupled to the gantry. The detector assembly comprises a detector driver that shifts the detector laterally with respect to a frame of the detector assembly to the desired position. The second position 80 has a minimal overlap 82 with the first position 2, enabling a detector offset 84 that is greater than can be achieved with conventional systems (e.g., as shown in FIG. 1).

Although shown in FIG. 4 as being centered relative to the center beam 1, in embodiments, when in the first position, the detector 34 may be not centered relative to the center beam 1, although the center beam 1 is captured by the detector 34. In such embodiments, second position 80 has a minimal overlap 82 with the first position 2. Accordingly, in various embodiments, when in the first position, the detector 34 interacts with the center beam 1 of the radiation source and, when in the second position, the detector 34 does not interact with the center beam of the radiation source, but overlaps the first position.

As will be described in greater detail below, the lateral movement of the detector 34 in combination with the dual scanning capabilities of the multimodal apparatus 10 results in two sets of data that, when combined, provide a complete dataset that can be used, for example, to provide a complete patient scan while reducing or even avoiding transaxial truncation.

As shown in FIG. 3, the multimodal apparatus 10 may be integrated with a radiotherapy device that includes a high-energy radiation source (e.g., MV) 20 coupled to or otherwise supported by the rotatable gantry 12. In accordance with one embodiment, the high-energy radiation source 20 is configured as a source of therapeutic radiation, such as a high-energy source of radiation used for treatment of a tumor within a patient in a region of interest. In other embodiments, the high-energy radiation source 20 is also configured as a source of imaging radiation, or at least utilized as such. It will be appreciated that the source of therapeutic radiation can be a high-energy x-ray beam (e.g., MV x-ray beam), and/or a high-energy particle beam (e.g., a beam of electrons, a beam of protons, or a beam of heavier ions, such as carbon) or another suitable form of high-energy radiation. In one embodiment, the high-energy radiation source 20 comprises a mega-electron volt peak photon energy (MeV) of 1 MeV or greater. In one embodiment, the high-energy x-ray beam has an average energy greater than about 0.8 MeV. In another embodiment, the high-energy x-ray beam has an average energy greater than about 0.2 MeV. In another embodiment, the high-energy x-ray beam has an average energy greater than about 150 keV. Generally, the high-energy radiation source 20 has a higher energy level (peak and/or average, etc.) than the low-energy radiation source 30.

In one embodiment, the high-energy radiation source 20 is a LINAC producing therapeutic radiation (e.g., MV) and the imaging system comprises an independent low-energy radiation source 30 producing relatively low intensity and lower energy imaging radiation (e.g., kV). In other embodiments, the therapeutic radiation source 20 could be a radioisotope, such as, for example, Co-60, which can generally have energy of greater than about 1 MeV. The high-energy radiation source 20 can emit one or more beams of radiation (indicated generally by 22) toward a region-of-interest (ROI) within a patient supported on the patient support 18 in accordance with a treatment plan.

In various embodiments, the high-energy radiation source 20 is utilized as a source of therapeutic radiation and a source of imaging radiation. As discussed in detail below, sources of radiation 20, 30 may be used in conjunction with one another to provide higher quality and better utilized images. References to the therapeutic radiation source 20 herein are to distinguish the high-energy radiation source 20 from the low-energy radiation source 30, which may be used only for imaging. However, references to the therapeutic radiation source 20 include embodiments where the therapeutic radiation source 20 (high-energy radiation source) can be utilized for therapy and/or imaging. In other embodiments, at least one additional radiation source can be coupled to the rotatable gantry 12 and operated to acquire projection data at a peak photon energy distinct from the peak photon energies of sources of radiation 20, 30.

Detector 24 can be coupled to or otherwise supported by the rotatable gantry 12 and positioned to receive radiation 22 from the therapeutic radiation source 20. The detector 24 can detect or otherwise measure the amount of radiation not attenuated and therefore infer what was in fact attenuated by the patient or associated patient ROI (by comparison to what was initially generated). The detector 24 can detect or otherwise collect attenuation data from different angles as the therapeutic radiation source 20 rotates around and emits radiation toward the patient.

It will be further appreciated that the therapeutic radiation source 20 can include or otherwise be associated with a beamformer or collimator. The beamformer associated with the therapeutic radiation source 20 can be configured in a number of ways, similar to the beamformer 36 associated with the imaging source 30. For example, a beamformer can be configured as a multi-leaf collimator (MLC), which can include a plurality of interlaced leaves operable to move to one or more positions between a minimally-open or closed position and a maximally-open position. It will be appreciated that the leaves can be moved into desired positions to achieve a desired shape of a radiation beam being emitted by the radiation source. In one embodiment, the MLC is capable of sub-millimeter targeting precision.

The therapeutic radiation source 20 may be mounted, configured, and/or moved into the same plane or a different plane (offset) than the imaging source 30. In some embodiments, scatter caused by simultaneous activation of the radiation sources 20, 30 may be reduced by offsetting the radiation planes.

In other embodiments, scatter can be avoided by interleaving the activations. For example, with simultaneous multimodal imaging, the acquisitions can be concurrent, without having concurrent individual pulses. In another embodiment, use of shadow-based scatter correction can be used, for example, to address the problem of MV scatter on a kV detector.

When integrated with a radiotherapy device, multimodal apparatus 10 can provide images that are used to set up (e.g., align and/or register), plan, and/or guide a radiation delivery procedure (treatment). Typical set-up is accomplished by comparing current (in-treatment) images to pre-treatment image information. Pre-treatment image information may comprise, for example, CT data, cone-beam CT data, MRI data, PET data or 3D rotational angiography (3DRA) data, and/or any information obtained from these or other imaging modalities. In some embodiments, the multimodal apparatus 10 can track in-treatment patient, target, or ROI motion.

A reconstruction processor 40 can be operatively coupled to detector 24 and/or detector 34. In one embodiment, the reconstruction processor 40 is configured to generate patient images based on radiation received by the detectors 24, 34 from the radiation sources 20, 30. It will be appreciated that the reconstruction processor 40 can be configured to be used to carry out the methods described more fully below. The apparatus 10 can also include a memory 44 suitable for storing information, including, but not limited to, processing and reconstruction algorithms and software, imaging parameters, image data from a prior or otherwise previously-acquired image (e.g., a planning image), treatment plans, and the like.

The multimodal apparatus 10 can include an operator/user interface 48, where an operator of the apparatus 10 can interact with or otherwise control the apparatus 10 to provide input relating to scan or imaging parameters and the like. The operator interface 48 can include any suitable input devices, such as a keyboard, mouse, voice-activated controller, or the like. The apparatus 10 can also include a display 52 or other human-readable element to provide output to the operator of the apparatus 10. For example, the display 52 can allow the operator to observe reconstructed patient images and other information, such as imaging or scan parameters, related to operation of the apparatus 10.

As shown in FIG. 3, the multimodal apparatus 10 includes a controller (indicated generally as 60) operatively coupled to one or more components of the apparatus 10. The controller 60 controls the overall functioning and operation of apparatus 10, including providing power and timing signals to the x-ray source 30 and/or the therapeutic radiation source 20 and a gantry motor controller that controls rotational speed and position of the rotatable gantry 12. It will be appreciated that the controller 60 can encompass one or more of the following: a patient support controller, a gantry controller, a controller coupled to the therapeutic radiation source 20 and/or the x-ray source 30, a beamformer controller, a controller coupled to the detector 24 and/or the x-ray detector 34, and the like. In one embodiment, the controller 60 is a system controller that can control other components, devices, and/or controllers.

In various embodiments, the reconstruction processor 40, the operator interface 48, the display 52, the controller 60 and/or other components may be combined into one or more components or devices.

The apparatus 10 may include various components, logic, and software. In one embodiment, the controller 60 comprises a processor, a memory, and software. By way of example and not limitation, a multimodal apparatus and/or radiotherapy system can include various other devices and components (e.g., gantries, radiation sources, collimators, detectors, controllers, power sources, patient supports, among others) that can implement one or more routines or steps related to imaging and/or IGRT for a specific application, wherein a routine can include imaging, image-based pre-delivery steps, and/or treatment delivery, including respective device settings, configurations, and/or positions (e.g., paths/trajectories), which may be stored in memory. Furthermore, the controller(s) can directly or indirectly control one or more devices and/or components in accordance with one or more routines or processes stored in memory. An example of direct control is the setting of various radiation source or collimator parameters (power, speed, position, timing, modulation, etc.) associated with imaging or treatment. An example of indirect control is the communication of position, path, speed, etc. to a patient support controller or other peripheral device. The hierarchy of the various controllers that may be associated with the apparatus can be arranged in any suitable manner to communicate the appropriate commands and/or information to the desired devices and components.

Moreover, those skilled in the art will appreciate that the systems and methods may be implemented with other computer system configurations. The illustrated aspects of the invention may be practiced in distributed computing environments where certain tasks are performed by local or remote processing devices that are linked through a communications network. For example, in one embodiment, the reconstruction processor 40 may be associated with a separate system. In a distributed computing environment, program modules may be located in both local and remote memory storage devices. For instance, a remote database, a local database, a cloud-computing platform, a cloud database, or a combination thereof can be utilized with apparatus 10.

Multimodal apparatus 10 can utilize an exemplary environment for implementing various aspects of the invention including a computer, wherein the computer includes the controller 60 (e.g., including a processor and a memory, which may be memory 44) and a system bus. The system bus can couple system components including, but not limited to the memory to the processor, and can communicate with other systems, controllers, components, devices, and processors. Memory can include read only memory (ROM), random access memory (RAM), hard drives, flash drives, and any other form of computer readable media. Memory can store various software and data, including routines and parameters, which may comprise, for example, a treatment plan.

The therapeutic radiation source 20 and/or x-ray source 30 can be operatively coupled to a controller 60 configured to control the relative operation of the therapeutic radiation source 20 and the x-ray source 30. For example, the x-ray source 30 can be controlled and operated simultaneously with the therapeutic radiation source 20. In addition, or alternatively, the x-ray source 30 can be controlled and operated sequentially with the therapeutic radiation source 20, depending on the particular treatment and/or imaging plan being implemented. For example, in various embodiments, the radiation sources 20, 30 can be operated such that the measured projection data from the radiation sources 20, 30 are acquired simultaneously (or essentially/nearly (quasi-) simultaneous, e.g., within about 50 ms of each other) or sequentially (e.g., separated by seconds, minutes, etc.).

It will be appreciated that radiation sources 20, 30 and detector(s) 24, 34 can be configured to provide rotation around the patient during an imaging and/or treatment scan in a number of ways. In one embodiment, synchronizing the motion and exposure of the source 20, 30 with the longitudinal motion of the patient support 18 can provide a continuous helical acquisition or scan of a patient image during a procedure. In addition to continuous rotation of the radiation sources 20, 30 and detector(s) 24, 34 (e.g., continuous and constant rotation of the gantry with constant patient motion speed), it will be appreciated that other variations can be employed without departing from the scope of the disclosed technology. For example, the rotatable gantry 12 and patient support can be controlled such that the gantry 12 rotates in a "back-and-forth" manner (e.g., alternating clockwise rotation and counterclockwise rotation) around a patient supported on the patient support (as opposed to continuously, as is described above) as the support is controlled to move (at a constant or variable speed) relative to the rotatable gantry 12. In another embodiment, with successive step-and-shoot circular scans, movement of the patient support 18 in the longitudinal direction (step) alternates with a scanning revolution by the rotatable gantry 12 (shoot) until the desired volume is captured. The multimodal apparatus 10 is capable of volume-based and planar-based imaging acquisitions. For example, in various embodiments, the multimodal apparatus 10 may be used to acquire volume images and/or planar images and execute the associated processing.

In various embodiments, the detector 34 is moved between the first position 2 and the second position 80 (FIG. 4) between the scans. For example, in various embodiments, the detector 34 may be positioned in the first position 2 during a first helical scan and in the second position 80 during a second helical scan, or in the first position 2 while the patient support 18 moves in a first longitudinal direction and in the second position 80 while the patient support moves in a second, opposite, longitudinal direction. In embodiments, the same radiation source and the same trajectory of the radiation source is used for the first helical scan and the second helical scan. In other embodiments, the same radiation source is used for the first helical scan and the second helical scan, and one helical scan uses a right-hand helix trajectory while the other helical scan uses a left-hand helix trajectory. Movement of the detector 34 between the first and second positions can enable the multimodal apparatus 10 to acquire data using an extended FOV as provided in the imaging and automatic FOV selection processes described below.

Figure 5A:
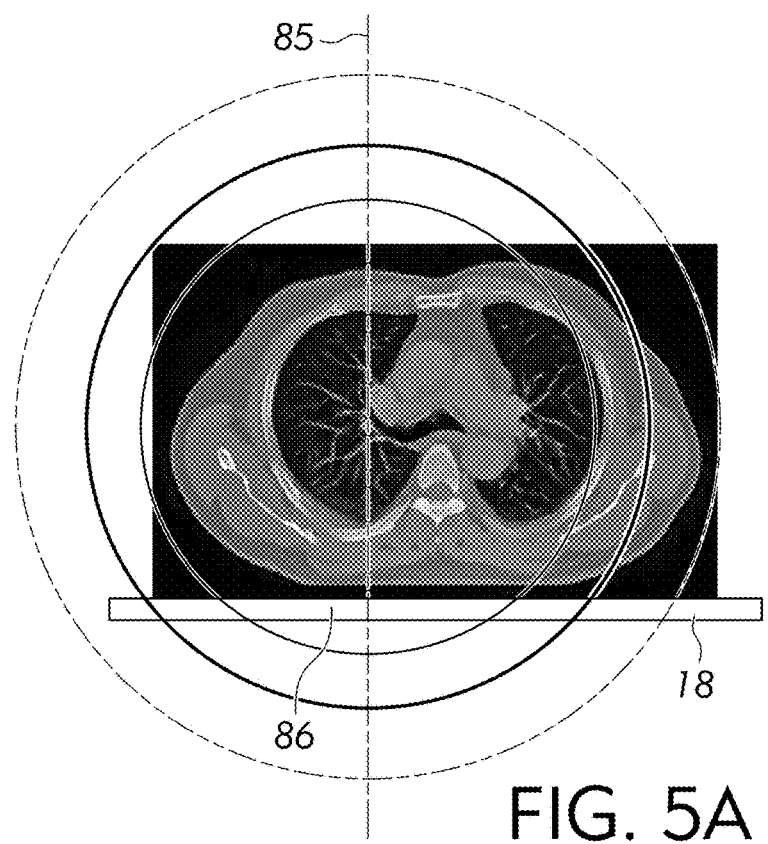
FIG. 5A is a diagrammatic illustration of a patient support configuration in which the patient support is in a first position in accordance with one or more embodiments described herein.
Figure 5B:
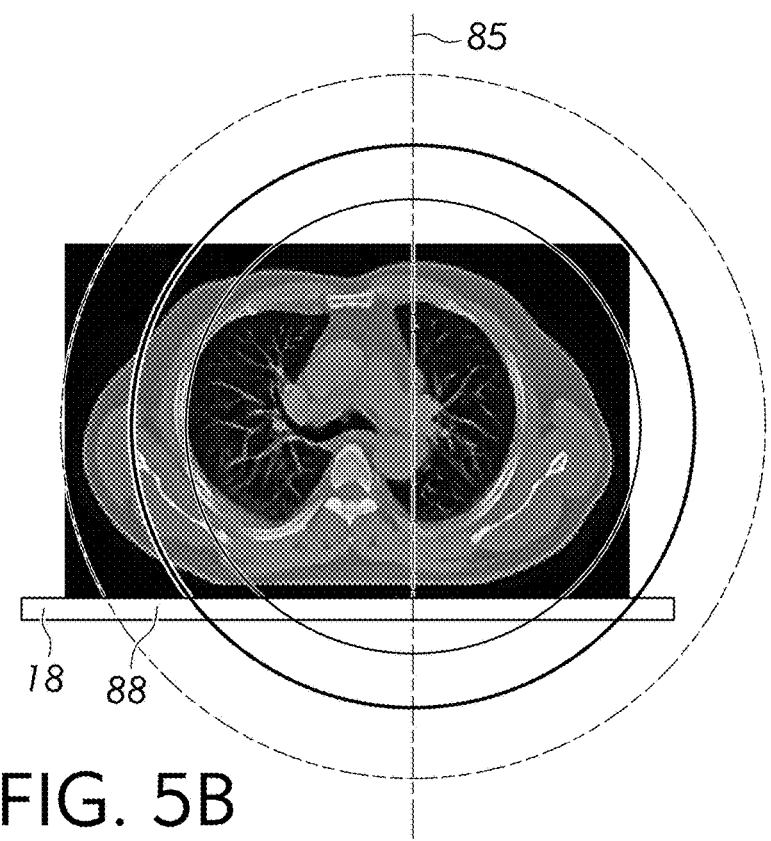
FIG. 5B is a diagrammatic illustration of a patient support configuration in which the patient support in FIG. 5A is moved to a second position in accordance with one or more embodiments described herein.

Although in various embodiments movement of the detector 34 from a first position 2 to a second position 80 is described, it is further contemplated that embodiments may employ lateral movement of the patient support 18 with respect to a central axis 85 of the gantry to achieve an extended FOV, as shown in FIGS. 5A and 5B. In FIG. 5A, the patient support 18 is in a first position 86 with respect to the central axis 85 of the gantry during a first scan. In embodiments, the first position 86 is offset relative to the central axis 85 of the gantry. The amount of offset can vary depending on the particular embodiment and may be, for example, limited by the internal diameter of the gantry bore 16 (FIGS. 2 and 3) and the lateral dimension of the detector 34. In some embodiments, the patient support 18 is centered with respect to the central axis 85 of the gantry in the first position 86.

Following the first scan, the patient support 18 is translated laterally to the second position 88, as shown in FIG. 5B. In FIG. 5B, the patient support 18 is offset relative to the central axis 85 of the gantry in the opposite direction. The amount of offset of the patient support 18 can be the same in the first and second directions, or the amount can be different, depending upon the size of the effective FOV to be achieved and the initial position of the patient on the patient support 18. A second scan is performed with the patient support 18 in the second position 88, and the two sets of data (e.g., the set of data from the first scan with the patient support in the first position and the set of data from the second scan with the patient support in the second position) are combined to provide a dataset that can be used, for example, to provide a patient scan while reducing or even avoiding transaxial truncation. Translation of the patient support 18 can enable the use of a detector with a smaller lateral dimension, which in turn can reduce costs and improve flexibility in system design.

During the first and second scans, the position of the detector can be the same in both scans, or can be different, depending on the particular embodiment. In other words, the patient support can be moved between first and second positions, the detector can be moved between first and second positions, or both, depending on the embodiment. As with other embodiments described herein, the first and second scans can be axial scans or helical scans. In embodiments, in which the scans are helical scans, the first scan is in a direction opposite a direction of the second scan.

Various other types of radiation source and/or patient support movement may be utilized to achieve relative motion of the radiation source and the patient for generation of projection data. Non-continuous motion of the radiation source and/or patient support, continuous but variable/non-constant (including linear and non-linear) movement, speed, and/or trajectories, etc., and combinations thereof may be used, including in combination with the various embodiments of apparatus 10 described above.

In one embodiment, the gantry 12 rotation speed, the patient support 18 speed, the beamformer shape, and/or the detector readout could all be constant during image acquisition. In other embodiments, one or more of these variables could change dynamically during image acquisition and/or treatment.

In other embodiments, these features can be combined with one or more other image-based activities or procedures, including, for example, patient set up, adaptive therapy monitoring, treatment planning, etc.

Figure 6:
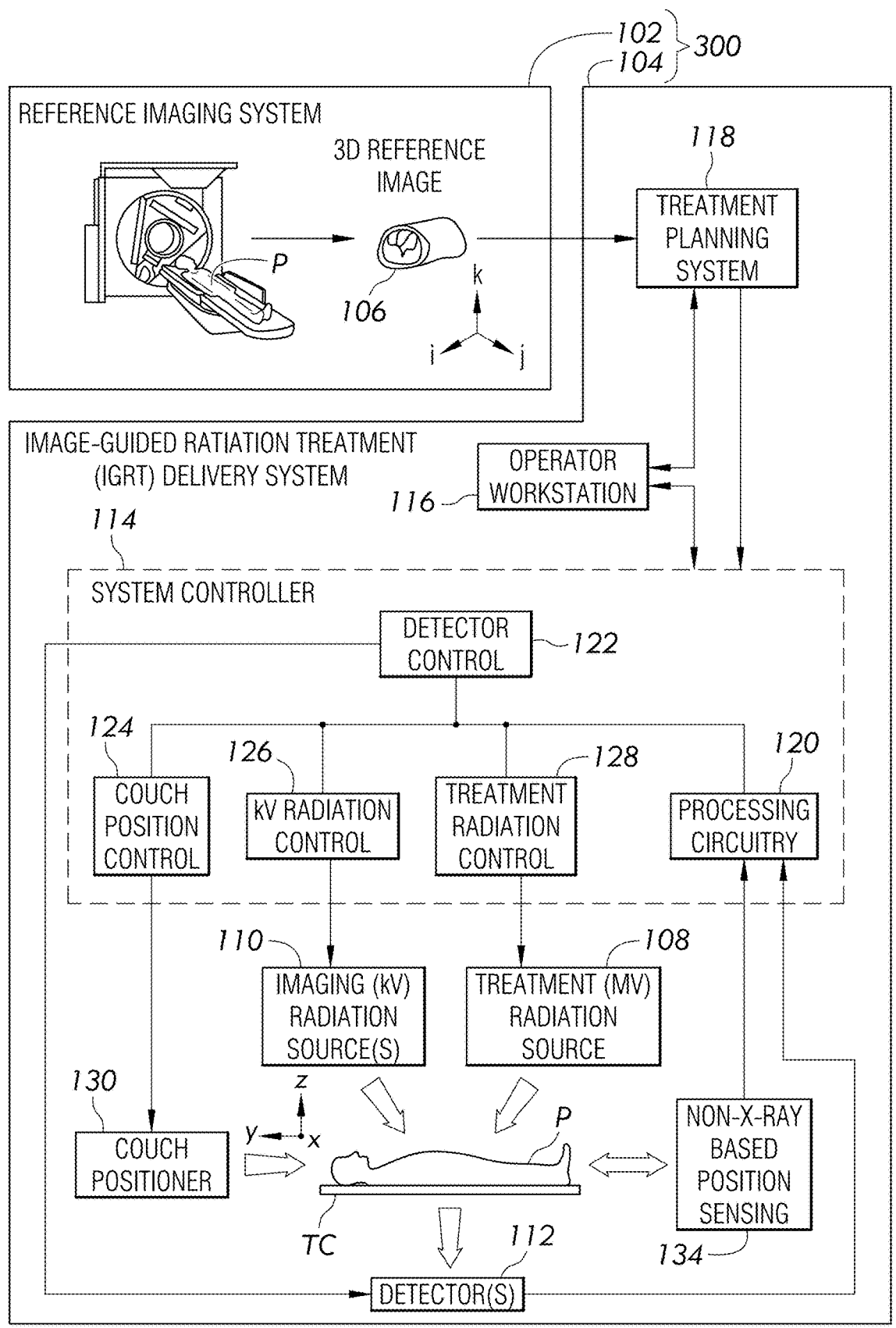
FIG. 6 illustrates an exemplary radiation treatment environment in accordance with one or more embodiments described herein.

FIG. 6 illustrates an exemplary radiation treatment environment 300. The radiation treatment environment 300 includes a reference imaging system 102 and an IGRT system 104. The IGRT system 104 may comprise, for example, the multimodal apparatus 10 and its various components and devices as described above.

In one embodiment, the reference imaging system 102 can include a high precision volumetric imaging system such as, for example, a CT system or a MRI system. In view of cost and workflow considerations in many clinical environments, the reference imaging system 102 is often a general purpose tool used for a variety of different purposes in the clinic or hospital environment, and is not specifically dedicated to the IGRT system 104 or environment 300. Rather, the reference imaging system 102 may be located in its own separate room or vault and is purchased, installed, and/or maintained on a separate and more generalized basis than the IGRT system 104. Accordingly, for the embodiment of FIG. 6, the reference imaging system 102 is illustrated as being distinct from the IGRT system 104. In other embodiments, the reference imaging system 102 may be considered an integral component of the IGRT system 104. For example, the multimodal apparatus 10 has the capability to act as the reference imaging system 102 and the IGRT system 104.

In this embodiment, IGRT system 104 comprises a high-energy radiation treatment (MV) source 108 that selectively applies high-energy x-ray treatment radiation to a target volume of a patient P positioned on a patient support or treatment couch TC. The MV source 108 applies the treatment radiation under the control of system controller 114, and in one embodiment, more particularly a treatment radiation control subsystem 128. System controller 114 further comprises processing circuitry 120, a detector controller 122, a couch position controller 124, and a kV radiation controller 126, each programmed and configured to achieve one or more of the functionalities described further herein. One or more imaging (kV) radiation sources 110 selectively emit relatively low-energy x-ray imaging radiation under the control of kV radiation controller 126, the imaging radiation being captured by one or more detectors 112. One or more of the detectors 112 can capture high-energy x-ray treatment radiation from MV source 108 that has propagated through the target volume.

Each kV radiation source 110 and the MV radiation source 108 have a precisely measurable and/or precisely determinable geometry relative to the (x, y, z) coordinate system of the IGRT system 104 and/or treatment room since they are dynamically moveable.

A couch positioner 130 can be actuated by the couch position controller 124 to position the couch TC. In some embodiments, a non-x-ray based position sensing system 134 senses position and/or movement of external marker(s) strategically affixed to the patient, and/or senses position and/or movement of the patient skin surface itself, using one or more methods that do not involve ionizing radiation, such as optically based or ultrasonically based methods. IGRT system 104 further includes an operator workstation 116 and a treatment planning system 118.

In common clinical practice, treatment planning is performed on a pre-acquired treatment planning image or prior image data 106 generated by the reference imaging system 102. The pre-acquired treatment planning image 106 is often a high-resolution three-dimensional CT image acquired substantially in advance (e.g., one to two days in advance) of the one or more radiation treatment fractions that the patient will undergo. As indicated in FIG. 6 by the illustration of an (i, j, k) coordinate system for the pre-acquired treatment planning image 106, which is in contrast to the (x, y, z) treatment room coordinate system illustrated for the treatment room of the IGRT system 104, there is generally no pre-existing or intrinsic alignment or registration between the treatment planning image 106 coordinate system and the treatment room coordinate system. During the treatment planning process, a physician typically establishes a coordinate system (e.g., i, j, k in treatment planning image 106) within the treatment planning image, which may also be referred to herein as the planning image coordinate system or planning image reference frame. A radiation treatment plan is developed in the planning image coordinate system that dictates the various orientations, sizes, durations, etc., of the high-energy treatment radiation beams to be applied by the MV source 108 during each treatment fraction. Accurate delivery of therapeutic radiation to a target requires aligning the planning image coordinate system with the treatment room coordinate system, as the entire delivery and tracking system (if present) is calibrated to the treatment room coordinate system. It will be appreciated that this alignment does not need to be exact and further appreciated that couch adjustment or beam delivery adjustment can be used to account for offsets in the alignment between the two coordinate systems.

In embodiments, the treatment planning image 106 can be used, for example, to determine that the maximum FOV from a conventional CBCT configuration (FIG. 1) is sufficient, while in other embodiments, the treatment planning image 106 can be used to determine that an extended FOV as described herein is needed. Accordingly, the treatment planning image 106 can be used to determine the FOV and, accordingly, a detector offset and/or a lateral translation of the patient support to be used during the treatment, if any.

For example, when the patient is supported on the patient support with a treatment target at approximately the isocenter of the system, the planning image position in the imaging geometry is determined. Based on the planning image, the system finds the body contour (e.g., the boundary) of the patient and calculates the largest distance from any point of the body contour to the isocenter in transaxial planes for the axial range of the scan. The body contour can be determined according to one of any known methods of detecting boundaries, including, but not limited to, simple segmentation or the like. In embodiments, the optimal FOV is twice the largest distance obtained plus a predetermined margin. Using the optimal FOV and the known size of the detector, the amount of detector offset is calculated. The size of the FOV and amount of detector offset can, therefore, be optimized to reduce or even prevent lateral (i.e., transaxial) truncation while improving detector usage and decreasing scanning time.

In one embodiment, immediately prior to each treatment fraction, under image guidance via the kV imaging radiation source(s) 110, including according to one or more of the embodiments described further herein below, image-based pre-delivery steps may be performed. For example, the patient can be physically positioned or aligned such that the planning image coordinate system (defined, for example and not by way of limitation, by a physician while creating a treatment plan on a CT image or planning image) is positioned into an initial alignment with the treatment room coordinate system, hereinafter termed an initial treatment alignment or initial treatment position. This alignment is commonly referred to as patient set up or patient alignment. Depending on the location of the target volume, the target volume can vary in position and orientation and/or can undergo volumetric deformations due to patient movement and/or physiological cycles such as respiration. As used herein, the term in-treatment alignment variation or in-treatment position variation is used to refer to the variations in position, orientation, and/or volumetric shape by which the current state of the target volume differs from the initial treatment alignment. By virtue of a known relationship between the treatment planning coordinate system and the treatment room coordinate system, the term in-treatment alignment variation can also be used to refer to the variations in position, orientation, or volumetric shape by which the current state of the target volume differs from that in the treatment planning coordinate system. More generally, the term initial treatment alignment or initial treatment position refers herein to the particular physical pose or disposition (including position, orientation and volumetric shape) of the body part of the patient upon patient setup at the outset of the treatment fraction.

A non x-ray based position sensing system 134 may also be provided. This non x-ray based position sensing system 134 may include, for example, external markers affixed in some manner to a patient's chest which move in response to respiration, which can precisely determine target location. Other mechanisms for monitoring respiration may also be used. Other non-respiratory position sensing systems 134 may also be used, including, for example, quasi static positioning, EKG for cardiac gating, etc. System 134 can correlate motion of the external markers with target motion, as determined from, for example, mono or stereoscopic x-ray projections. Non x-ray based position sensing system 134, therefore, can permit system controller 114 to monitor external marker motion, use the correlation model to precisely predict where the target will be located in real time (e.g., ~60 Hz), and direct the treatment beam to the target. As treatment of the moving target progresses, additional x-ray images may be obtained and used to verify and update the correlation model.

As used herein, "registration" of medical images refers to the determination of a mathematical relationship between corresponding anatomical or other (e.g. fiducial) features appearing in those medical images. Registration can include, but is not limited to, the determination of one or more spatial transformations that, when applied to one or both of the medical images, would cause an overlay of the corresponding anatomical features. The spatial transformations can include rigid-body transformations and/or deformable transformations and can, if the medical images are from different coordinate systems or reference frames, account for differences in those coordinate systems or reference frames. For cases in which the medical images are not acquired using the same imaging system and are not acquired at the same time, the registration process can include, but is not limited to, the determination of a first transformation that accounts for differences between the imaging modalities, imaging geometries, and/or frames of reference of the different imaging systems, together with the determination of a second transformation that accounts for underlying anatomical differences in the body part that may have taken place (e.g., positioning differences, overall movement, relative movement between different structures within the body part, overall deformations, localized deformations within the body part, and so forth) between acquisition times.

Registration of data for use in generating images may be implemented between the reference imaging system 102 and the IGRT delivery system 104 and/or between the data and/or images derived from the various modalities of the multimodal IGRT delivery system 104, including the low energy source(s) 110 and the high energy source 108 (and their associated detectors 112). In particular, referring back to apparatus 10, registration may be implemented between data and/or images derived from radiation sources 20, 30 and detectors 24, 34. Various embodiments described herein reduce transaxial truncation artifacts and quantitative bias due to the increased FOV, which in turn can improve registration accuracy.

In one embodiment, FIG. 7 shows an illustration of an exemplary multimodal scan configuration 400. Looking into the front of the ring gantry 410, FIG. 7 shows a high energy radiation source 420 (e.g., MV) and a low energy radiation source 430 (e.g., kV) mounted to the ring gantry 410. Radiation sources 420, 430 are shown mounted orthogonal to each other, but other embodiments can include other angular relationships and additional radiation sources and/or detectors. High energy radiation source 420 is shown projecting radiation through a beamformer 426 to create radiation beam 422 projecting onto a portion of detector 424. In this configuration, high energy radiation source 420 has transaxial field of view (FOV) 428. Low energy radiation source 430 is shown projecting radiation through a beamformer 436 to create radiation beam 432 projecting onto a portion of detector 434. In this configuration, low energy radiation source 430 has transaxial FOV 438. Detector 434 is shown centered within its range 435. In this manner, the radiation sources 420, 430 will project radiation through an overlapping transaxial FOV. In this embodiment, the multimodal scan configuration 400 shows the high energy FOV 428 with a larger transaxial FOV than the low energy FOV 438.

In another embodiment, FIG. 8 shows an illustration of another exemplary multimodal scan configuration 500. Looking into the front of the ring gantry 410, FIG. 8 also shows the high energy radiation source 420 and the low energy radiation source 430 mounted orthogonally to the ring gantry 410. High energy radiation source 420 is shown projecting radiation through a beamformer 526 to create radiation beam 522 projecting onto detector 524. In this configuration, high energy radiation source 420 has transaxial FOV 528. Low energy radiation source 430 is shown projecting radiation through a beamformer 536 to create radiation beam 532 projecting onto offset detector 534 (e.g., the detector is in the second position as in FIG. 4). The beamformer 536 also collimates the radiation from the low energy radiation source 430 to minimize the dose to the patient. In this configuration, the offset detector 534 has a minimal overlap with the position of the detector 434, and low energy radiation source 430 has transaxial FOV 538 with at least rotation of 180 degrees plus the fan angle span by the detector. The low energy radiation source 430 has a large angular coverage to cover the offset detector 534 with minimal overlap of the position of the detector 434. In various embodiments, the data obtained from the offset detector 534 can be combined with the data obtained from the detector 434 to provide a complete dataset.

Various factors, including, for example, beamformer configurations, radiation source angles, detector positions, etc. may be used to control the respective FOVs (e.g., transaxial and axial) of the radiation sources. In some embodiments, the radiation sources 420, 430 may be physically offset in the longitudinal direction (along the y-axis) and may scan the patient at different times (temporally offset).

In various embodiments, the first scan FOV and the second scan FOV provide overlapping imaging data. However, as described above, the first scan FOV and the second scan FOV can provide non-overlapping imaging data, or imaging data that is outside the other FOV. Overlapping imaging data between the first scan FOV and the second scan FOV can be used, for example, to register data and/or images and to achieve higher quality images in desired locations.

For example, for head/neck applications, a centered detector scan may typically be desired, but such a configuration has the smallest scan FOV, and data may be truncated. Although the amount of transaxial truncation may be small, software-based transaxial truncation compensation may lead to significant bias in the Hounsfield unit (HU) values of the projections, thereby making the projections and, thus, the reconstructed images, not quantitatively accurate for dose calculation and planning. Accordingly, in various embodiments described herein, the imaging data from the first scan (having the detector in the first position) and the imaging data from the second scan (having the detector in a second, offset position) can be combined, with the overlapping imaging data being sufficient to decrease bias in the reconstructed image, thereby enabling the reconstructed image to be used for dose calculation and planning. For example, when the two data sets are combined, they form a measured dataset with a larger FOV having significantly reduced transaxial truncation (e.g., as compared to each of the two data sets individually), or even without transaxial truncation. Images reconstructed from the dataset, therefore, can include reduced or even no bias as compared to images reconstructed from the individual data sets. Moreover, it should be appreciated that the use of a multimodal apparatus as described herein can enable the dose to be delivered in the same way as in a conventional scan, while the imaging detector is offset to enable an improved reconstructed image.

In some embodiments, one or more of the radiation sources may be used for sparse data, may utilize different resolutions, speeds, trajectories, frequencies, power levels, dosages, FOVs, etc. In any event, data from two or more radiation modalities can be used in combination to improve image quality, speed, dosing, workflow, treatment accuracy/precision, etc.

In various embodiments, the exemplary scan configurations 400, 500 may be implemented using multimodal apparatus 10, including via radiation treatment environment 300.

The following flow charts and block diagrams illustrate exemplary configurations and methodologies associated with the multimodal radiation systems described above. The exemplary methodologies may be carried out in logic, software, hardware, or combinations thereof. In addition, although the procedures and methods are presented in an order, the blocks may be performed in different orders, including series and/or parallel. Further, additional steps or fewer steps may be used.

Figure 9:
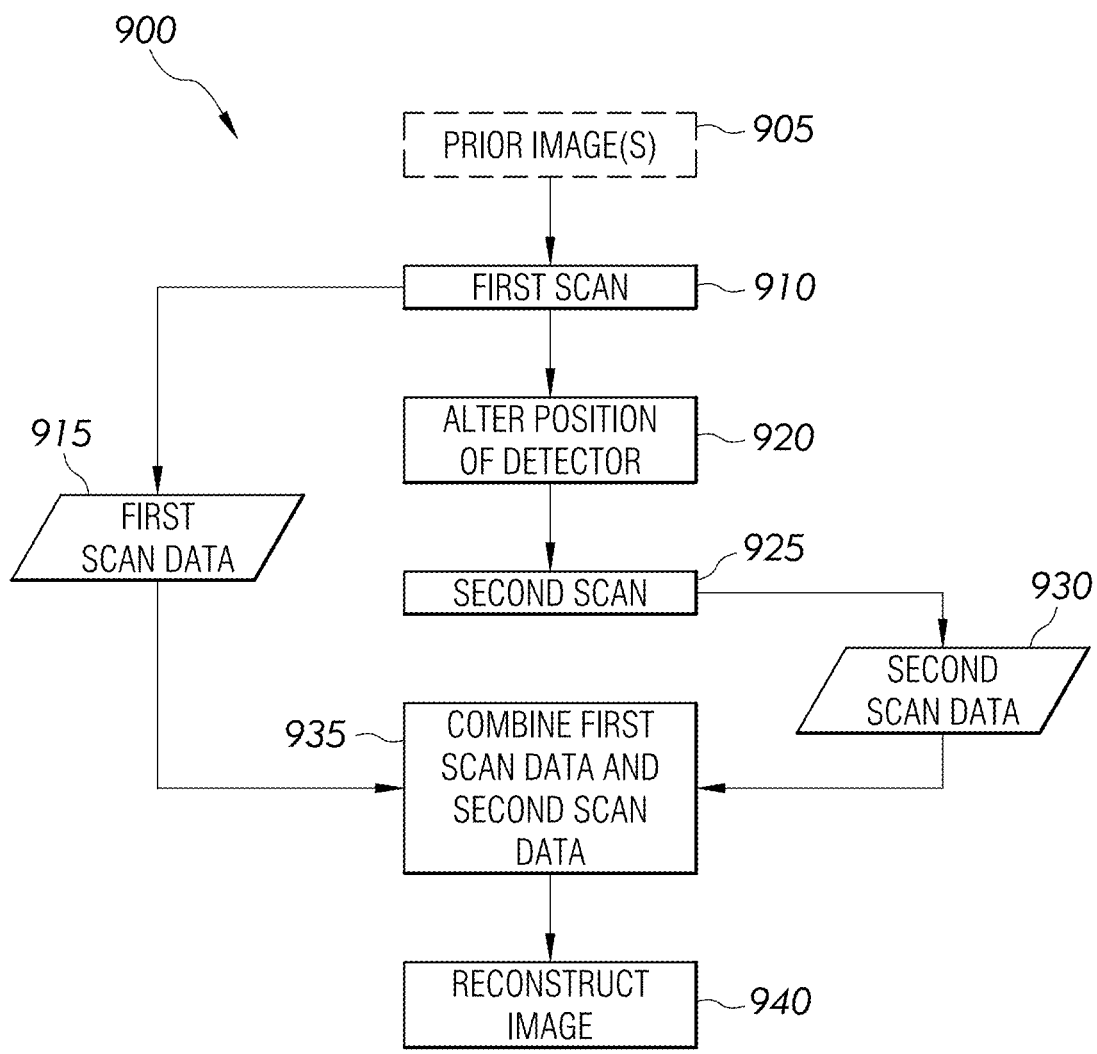
FIG. 9 is a flow chart depicting an exemplary method of combining scan data from multiple scans in which a detector is repositioned between scans in accordance with one or more embodiments described herein.

FIG. 9 is a flow chart depicting an exemplary method 900 of combining scan data from scans having different detector positions, such as those described above. At step 905, prior image data (e.g., data from a reference image 106) may be provided. At step 910, the method 900 executes a first scan. In embodiments, the first scan is a helical scan conducted with a scan configuration having the detector in a first, centered position, and the patient support moving in a first longitudinal direction (e.g., the y-direction in FIG. 2) relative to the gantry. In some embodiments, the first position of the detector may be off-set relative to the central beam of the radiation source. The scan produces first scan data 915. Next, at step 920, the method 900 alters the position of the detector. For example, the detector is laterally shifted with respect to the central beam from a first position to a second, offset position. The second, offset position of the detector partially overlaps the first position of the detector.

At step 925, the second scan is executed. In embodiments, the second scan is a helical scan conducted with a scan configuration having the detector in a second, offset position, and the patient support moving in a second longitudinal direction (e.g., the y-direction in FIG. 2) relative to the gantry, opposite the first longitudinal direction. In embodiments, the second scan has the same source trajectory as the source trajectory of the first scan. The scan produces second scan data 930. Then at step 935, the method 900 makes use of a dataset including the first scan data and the second scan data having reduced transaxial truncation (e.g., as compared to each of the first scan data and the second scan data alone) or without transaxial truncation.

In embodiments, at each particular view angle, the dataset includes data from three regions: a first region that is viewable only from the first position of the detector, a second region that is viewable only from the second position of the detector, and a third region between the first and second regions and is viewable from the overlap of the first and second positions of the detector. Data from the third region is generated by fusing projection data from the first and second positions of the detector such that the transitions from the first region to the third region and from the third region to the second region are smooth. In embodiments, fusion of the data can be achieved by applying complementary smooth weighting functions to projection data from the first and second positions of the detector in the third region.

At step 940, the method 900 processes the dataset, for example, to reconstruct an image. In this manner, generally, the scan configuration and associated scan designs can be configured such that at least one of the scan data 915, 930 complements or supplements another of the scan data 915, 930 from a different scan to yield at least one of the improvements discussed herein.

Figure 10:
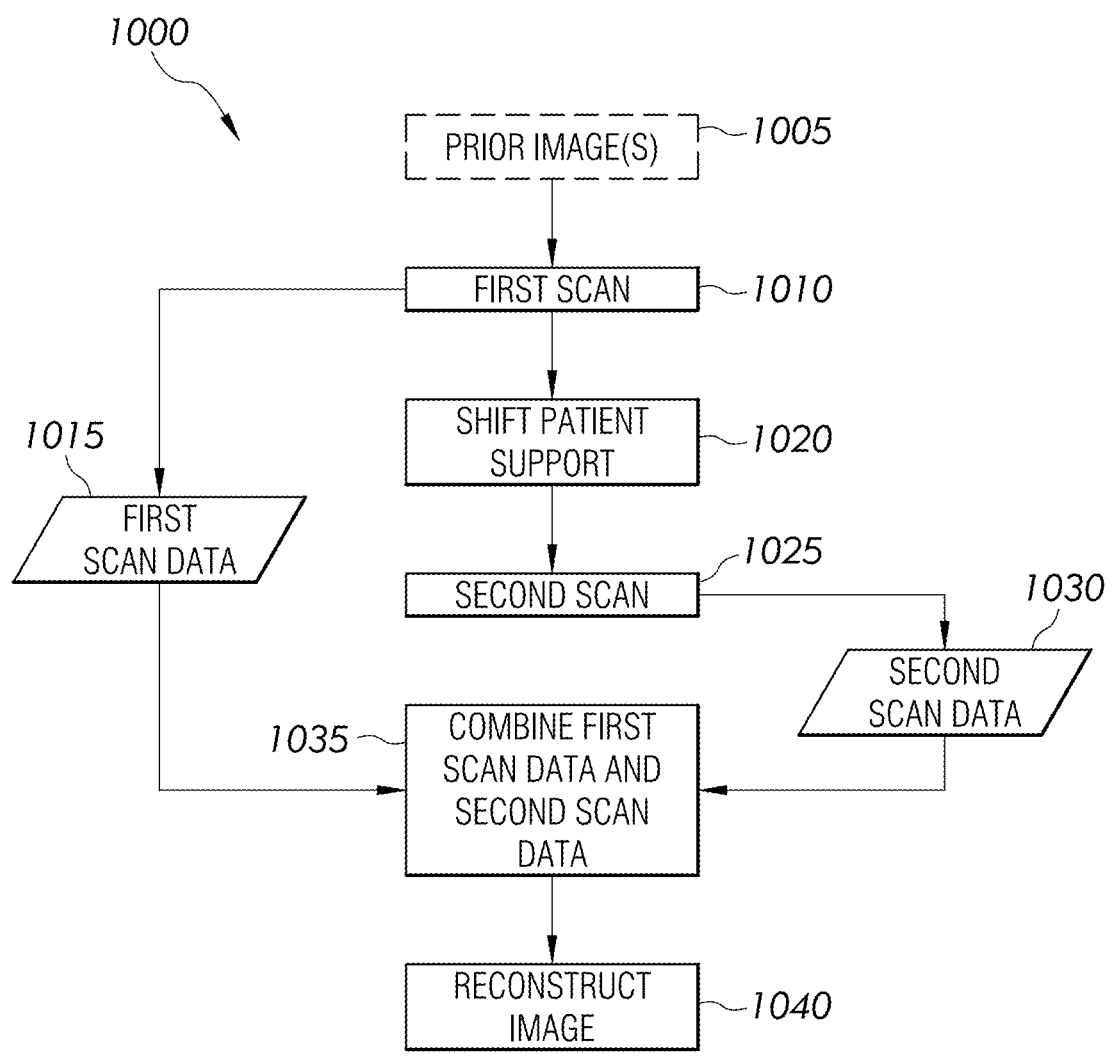
FIG. 10 is a flow chart depicting an exemplary method of combining scan data from multiple scans in which a patient support is repositioned between scans in accordance with one or more embodiments described herein.

FIG. 10 is a flow chart depicting an exemplary method 1000 of combining scan data from scans having different patient support positions, such as those described above. At step 1005, prior image data (e.g., data from a reference image 106) may be provided. At step 1010, the method 1000 executes a first scan. In embodiments, the first scan is a helical scan conducted with a scan configuration having the patient support in a first position relative to the central axis of the gantry, and the patient support moving in a first longitudinal direction (e.g., the y-direction in FIG. 2) relative to the gantry. The scan produces first scan data 1015. Next, at step 1020, the method 1000 shifts the patient support. For example, the patient support is laterally shifted with respect to the central axis of the gantry from the first position to a second position. As described hereinabove, although not shown, the detector may, in some embodiments, additionally be moved from a first position to a second position between the first scan and the second scan.

At step 1025, the second scan is executed. In embodiments, the second scan is a helical scan conducted with a scan configuration having the patient support in the second position, and moving in a second longitudinal direction (e.g., the y-direction in FIG. 2) relative to the gantry, opposite the first longitudinal direction. In embodiments, the second scan has the same source trajectory as the source trajectory of the first scan. The scan produces second scan data 1030. Then at step 1035, the method 1000 forms a dataset including the first scan data and the second scan data.

In embodiments, the first scan data is virtually mapped to the second scan data in the dataset such that the second scan data represents the same lateral object position as the first scan data in the resultant dataset. For example, information regarding the scan geometry, x-ray spectrum, and the detector response can be used to virtually map the first scan data to the second scan data.

In embodiments, at each particular view angle, the dataset includes data from three regions: a first region that is viewable only when the patient support is in the first position, a second region that is viewable only when the patient support is in the second position, and a third region between the first and second regions and is viewable when the patient support is in the first position and when the patient support is in the second position (e.g., the overlap of the first and second positions). Data from the third region is generated by fusing projection data from the first and second scans such that the transitions from the first region to the third region and from the third region to the second region are smooth. In embodiments, fusion of the data can be achieved by applying complementary smooth weighting functions to projection data from the first and second scans in the third region.

At step 1040, the method 1000 processes the dataset, for example, to reconstruct an image. In this manner, generally, the scan configuration and associated scan designs can be configured such that at least one of the scan data 1015, 1030 complements or supplements another of the scan data 1015, 1030 from a different scan to yield at least one of the improvements discussed herein.

Figure 11:
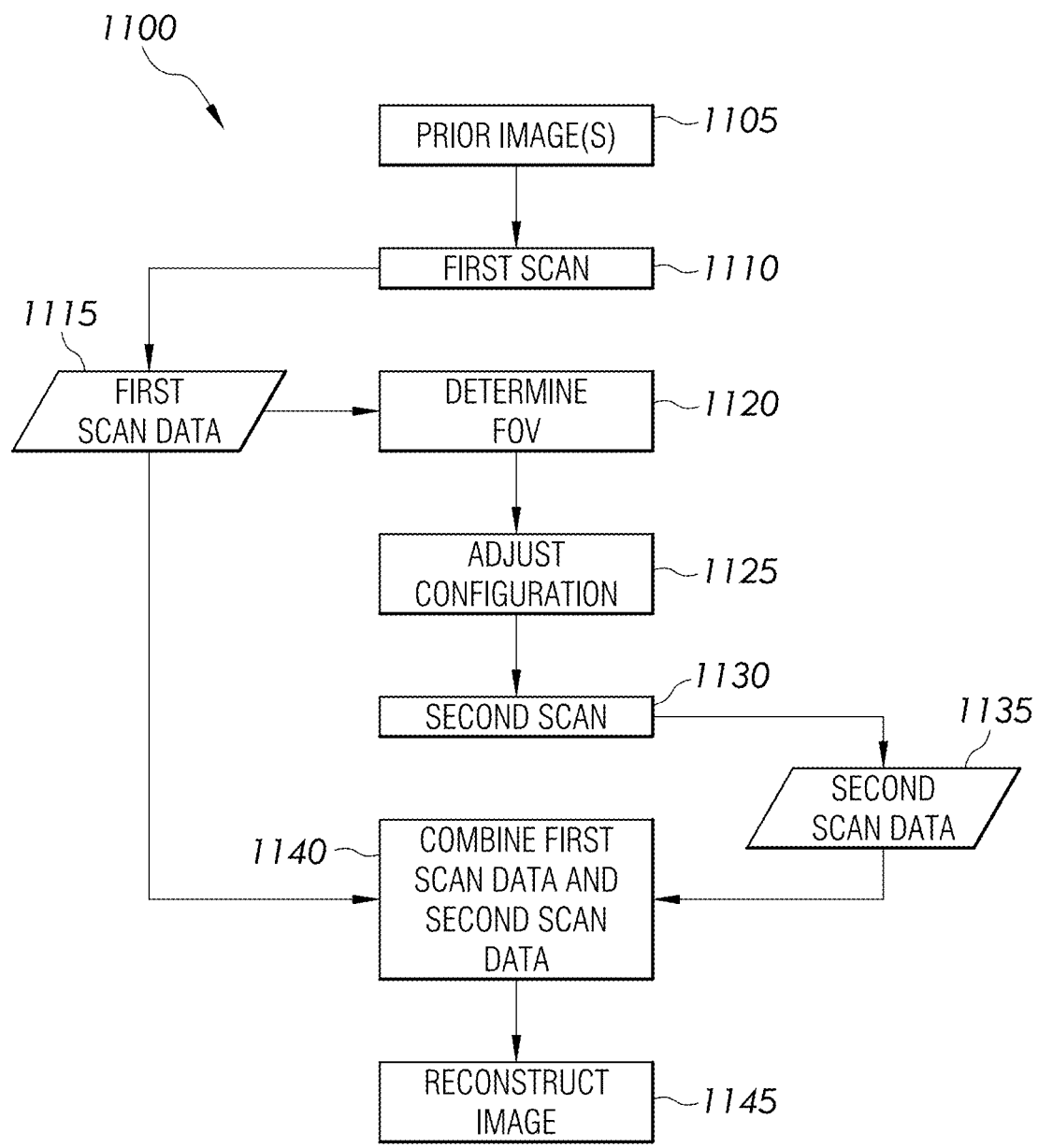
FIG. 11 is a flow chart depicting an exemplary method of using scan data to determine a FOV and adjust a configuration for a subsequent scan in accordance with one or more embodiments described herein

FIG. 11 is a flow chart depicting an exemplary method 1100 of using data from a prior image to automatically determine an optimal FOV and an amount of detector offset. At step 1105, prior image data (e.g., data from a reference image 106 or from a previous scan) is provided. Next, at step 1110, the method 1100 executes a first scan. In embodiments, the first scan is a helical scan conducted with a scan configuration having the detector in a first position relative to the center beam, and the patient support moving in a first longitudinal direction (e.g., the y-direction in FIG. 2) relative to the gantry. The scan produces first scan data 1115.

Next, at step 1120, the method 1100 determines an optimal FOV based on the prior image data and the first scan data. For example, by overlaying the prior image with the first image data and the FOV for the first scan, an optimal FOV may be selected. Selection of the optimal FOV can take into account, for example, the position of the patient with respect to the FOV, an application for the image data, an amount of transaxial truncation observed using the FOV for the first scan, the time to complete the scan, the amount of unused detector area, and the like. In embodiments, the optimal FOV can be determined manually, such as by displaying an overlay of the prior image with the first image data and the FOV for the first scan on a user interface and receiving FOV input from the user, or the optimal FOV can be determined automatically, such as by using the system controller 114 to select a FOV that eliminates or minimizes transaxial truncation without increasing an amount of unused detector area. In embodiments, software configured to identify a patient contour/boundary within the region of imaging may be used to determine the optimal field of view by comparing the boundaries or contours of the patient to the current FOV and identifying a position of the patient within the FOV. Based on the position of the patient within the FOV, in embodiments, a final FOV size can be determined, and an amount of detector or patient support shift can be calculated, for example, using software.

At step 1125, the method 1100 adjusts the configuration, such as by moving the detector from the first position to a second, offset position, or by laterally moving the patient support from a first position to a second position. In embodiments, the configuration may be adjusted to a conventional extended FOV position (e.g., as described in FIG. 1), or the configuration may be adjusted according to one or more embodiments described herein to enable an extra large FOV. In some embodiments, adjusting the configuration can include moving the patient support with respect to the detector. For example, in embodiments, the patient support may be moved laterally as described herein, or even up or down, to improve the position of the patient within the FOV for the first scan.

Moreover, in embodiments, the dose of radiation to the patient due to the imaging scans may be optimized based on the first scan data and the prior image data, as described herein. In particular, the radiation dose due to the imaging scans increases as the portion of the patient's body that is exposed to the x-ray increases given the same scan settings. However, optimization of the FOV can determine the optimal overlap of the patient body in two scans, thereby allowing the minimization or optimization of the total dose from the radiation source to the patient. Additionally, by using an optimized FOV and a balanced signal for imaging, the scan mA can be reduced for one or both of the scans, thereby enabling the total dose to be reduced.

At step 1130, the second scan is executed. In embodiments, the second scan is a helical scan conducted with a scan configuration having the patient support in the second position, and moving in a second longitudinal direction (e.g., the y-direction in FIG. 2) relative to the gantry, opposite the first longitudinal direction. The scan produces second scan data 1135. Then at step 1140, the method 1100 makes use of a dataset including the first scan data and the second scan data. At step 1145, the method 1100 processes the dataset, for example, to reconstruct an image. In this manner, generally, the scan configuration and associated scan designs can be configured such that at least one of the scan data 1115, 1135 complements or supplements another of the scan data 1115, 1135 from a different scan to yield at least one of the improvements discussed herein. In embodiments, the reconstructed image may have an image quality that is improved as compared to conventional methods, or may have a similar image quality as compared to conventional methods with less scanning time.

In various embodiments, it is further contemplated that high energy MV fan-beam projections and low energy kV fan-beam or cone-beam projections can be used in image reconstructions. In some embodiments, the MV projections can be used as a priori information to amend artifacts of the kVCT, or used in a dual-energy CT reconstruction for quantitative imaging and material separation. Furthermore, MLC-modulated MV projection data is available during treatment and may be leveraged in kVCT reconstructions concurrent with or following treatment delivery. The kV acquisition can be concurrent with and/or preceding treatment. Electron density images obtained from dual-energy reconstructions can be used in both online and offline dosimetry applications.

Several issues that arise in known medical imaging and/or radiation treatment systems are at least partially addressed by one or more of the embodiments described herein. For example, various embodiments described herein can reduce or even eliminate lateral (i.e., transaxial) truncation, enable automatic FOV selection and configuration using information from an earlier scan or prior image, and deliver images having improved quality, thereby making such images suitable for use in treatment planning and dose calculation.

Various embodiments may further enable smaller detectors to be used within a multimodal apparatus without sacrificing the FOV of the apparatus.

In some embodiments, the above methods can be executed simultaneously or in an interleaved manner based on a preferred workflow. For example, a multimodal scan can be performed and the resulting scan data utilized for two or more of the various features and benefits described above.

When the above apparatus and methods are used in the projection domain, it can be applied on each projection view, where each projection view is a planar image. Various embodiments can utilize different scan geometries, detector positioning (including offset detectors), and/or beamformer window shapes.

In some embodiments, it will be appreciated that any potential increased scan time associated with multiple beam rotations to complete a volume image can be mitigated or otherwise offset by high kV frame rates, high gantry rates, and/or sparse data reconstruction techniques. It will be further appreciated that the above-described provision of a selectively controllable collimator/beamformer allows for a system where a user can trade off or otherwise vary image acquisition time versus image quality, depending on the specific application and/or clinical need. It also will be appreciated that the radiotherapy delivery device can be controlled to provide half- or single-rotation cone beam CT scans (with potential reduced image quality) with fast image acquisition time (e.g., for motion tracking), as well as circular or continuous helical acquisition with a narrow/slit fan beam with longer acquisition time, but increased image quality. One or more optimization processes are also applicable to all of the above embodiments to determine scan designs, determine beam positioning, determine readout range, estimate scatter, etc.

Although the disclosed technology has been shown and described with respect to a certain aspect, embodiment or embodiments, it is obvious that equivalent alterations and modifications will occur to others skilled in the art upon the reading and understanding of this specification and the annexed drawings. In particular regard to the various functions performed by the above described elements (components, assemblies, devices, members, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary aspect, embodiment or embodiments of the disclosed technology. In addition, while a particular feature of the disclosed technology may have been described above with respect to only one or more of several illustrated aspects or embodiments, such feature may be combined with one or more other features of the other embodiments, as may be desired and advantageous for any given or particular application.

While the embodiments discussed herein have been related to the systems and methods discussed above, these embodiments are intended to be exemplary and are not intended to limit the applicability of these embodiments to only those discussions set forth herein. While the present invention has been illustrated by the description of embodiments thereof, and while the embodiments have been described in some detail, it is not the intention of the applicant to restrict or in any way limit the scope of the appended claims to such detail. Additional advantages and modifications will readily appear to those skilled in the art.

Therefore, the invention in its broader aspects is not limited to the specific details, representative apparatus and methods, and illustrative examples shown and described. Accordingly, departures may be made from such details without departing from the spirit or scope of the applicant's general inventive concept.

The invention claimed is:

1. An imaging apparatus, comprising:
a rotatable gantry system positioned at least partially around a patient support;
a first source of radiation coupled to the rotatable gantry system, the first source of radiation configured for imaging radiation;
a second source of radiation coupled to the rotatable gantry system; and
a first radiation detector coupled to the rotatable gantry system and laterally movable relative to a central beam of the first source of radiation to receive radiation from at least the first source of radiation over various fields of view for a particular view angle;
wherein first scan data is acquired during a first scan, second scan data is acquired during a second scan, and the first scan data and the second scan data are combined to provide a dataset corresponding to an effective field of view of the imaging apparatus that is greater than any of the various fields of view individually;
wherein the first scan comprises a first helical scan and the second scan comprises a second helical scan; and
wherein the patient support is moved in a transaxial plane between the first scan and the second scan.

2. The imaging apparatus according to claim 1, wherein:
the first radiation detector is in a first position during the first scan; and
the first radiation detector is in a second position during the second scan, and
the first position and the second position have a lateral overlap.

3. The imaging apparatus according to claim 1, further comprising a reconstruction processor configured to generate a reconstructed image based on a dataset comprising the first scan data and the second scan data, wherein the dataset has reduced transaxial truncation as compared to each of the first scan data and the second scan data.

4. The imaging apparatus of claim 1, wherein at least one of the first source of radiation or the second source of radiation is configured to produce a cone beam geometry.

5. The imaging apparatus of claim 1, wherein the second source of radiation is configured as a source of therapeutic radiation.

6. An imaging apparatus, comprising:
a gantry system rotatable about a central axis and at least partially surrounding a patient support;
a source of radiation coupled to the gantry system; and
a radiation detector coupled to the rotatable gantry system and laterally movable between a first position in which the radiation detector interacts with a central beam of the source of radiation, and a second position in which the radiation detector does not interact with the central beam of the source of radiation, wherein the first position and the second position have lateral overlap and wherein the radiation detector receives radiation from the source of radiation at a particular view angle in the first position and the second position; and
wherein the patient support is moved in a transaxial plane from one position when the radiation detector is in the first position to another position when the radiation detector is in the second position.

7. The imaging apparatus according to claim 6, wherein first scan data is acquired during a first scan with the detector at the first position and the patient support at the one position, second scan data is acquired during a second scan with the detector at the second position and the patient support at the another position, and the first scan data and the second scan data are combined to provide a dataset corresponding to an effective field of view of the imaging apparatus that is greater than any of the various fields of view individually.

8. The imaging apparatus according to claim 6, further comprising a reconstruction processor configured to generate a reconstructed image based on a dataset comprising first scan data acquired during a first scan with the detector at the first position and second scan data acquired during a second scan with the detector at the second position, wherein the dataset has reduced transaxial truncation as compared to the first scan data and the second scan data or no transaxial truncation.

9. The imaging apparatus of claim 6, wherein the source of radiation is configured to produce a cone beam geometry.

10. The imaging apparatus of claim 6, wherein the source of radiation is a first source of radiation, and wherein the imaging apparatus further comprises a second source of radiation, the second source of radiation being configured as a source of therapeutic radiation.

11. The imaging apparatus of claim 10, wherein the second source of radiation has an energy level the same as or greater than the first source of radiation.

12. The imaging apparatus of claim 10, wherein the radiation detector comprises a flat panel radiation detector.

13. A method of using an imaging apparatus, comprising:
receiving data corresponding to an image of a patient positioned on a patient support;
receiving first scan data from a source of radiation at a radiation detector, the source of radiation configured for imaging radiation, wherein the first scan data comprises a scan field of view (FOV) and the first scan data is acquired during a first scan while the radiation detector is in a first position relative to a central beam of the source of radiation and the patient support is in a first position relative to a central axis of a rotatable gantry system that at least partially surrounds the patient support;
selecting an effective FOV based on the received data corresponding to the image and the first scan data, wherein the effective FOV is selected to minimize transaxial truncation in a projection of the patient; and
determining a second position of at least the patient support with respect to the central axis of the rotatable gantry system based on the selected effective FOV, wherein the second position is laterally offset from the first position.

14. The method according to claim 13, further comprising:
receiving second scan data from the source of radiation at the radiation detector, the second scan data being acquired during a second scan while the patient support is in the second position.

15. The method according to claim 14, further comprising generating a reconstructed image based on a dataset comprising the first scan data and the second scan data, wherein the dataset is within the effective FOV and has reduced transaxial truncation as compared to the first scan data and the second scan data or has no transaxial truncation.

16. The method according to claim 14, the first scan comprising a first helical scan, the second scan comprising a second helical scan, wherein the patient support moves in first longitudinal direction relative to the rotatable gantry system during the first helical scan, and in a second longitudinal direction relative to the rotatable gantry system during the second helical scan, the second longitudinal direction being opposite the first longitudinal direction.

17. The method according to claim 14, wherein the first scan data is acquired during the first scan while the radiation detector is in the first position and the second scan data is acquired during the second scan while the radiation detector is in the second position.

* * * * *